(12) United States Patent
Couto et al.

(10) Patent No.: US 6,200,560 B1
(45) Date of Patent: Mar. 13, 2001

(54) ADENO-ASSOCIATED VIRUS VECTORS FOR EXPRESSION OF FACTOR VIII BY TARGET CELLS

(75) Inventors: Linda B. Couto, Pleasanton; Peter C. Colosi; Xiaobing Qian, both of Alameda, all of CA (US)

(73) Assignee: Avigen, Inc., Alameda, CA (US)

( * ) Notice: Subject to any disclaimer, the term of this patent is extended or adjusted under 35 U.S.C. 154(b) by 0 days.

(21) Appl. No.: 09/470,618

(22) Filed: Dec. 22, 1999

Related U.S. Application Data

(63) Continuation-in-part of application No. 09/364,862, filed on Jul. 30, 1999.
(60) Provisional application No. 60/125,974, filed on Mar. 24, 1999, and provisional application No. 60/104,994, filed on Oct. 20, 1998.

(51) Int. Cl.[7] .......................... A61K 35/00; A61K 48/00; C12N 15/63; C12N 15/85; C12N 15/86
(52) U.S. Cl. ...................... 424/93.2; 435/320.1; 435/325; 435/456; 424/93.1; 514/44
(58) Field of Search ............................... 435/6, 69.1, 69.6, 435/320.1, 325, 366, 456; 514/44; 536/23.1, 23.5; 424/93.1, 93.2

(56) References Cited

PUBLICATIONS

Dodds et al. Molecular genetics, gene transfer, and therapy. Advances in Veterinary Medicine. vol. 40, pp. 119–135. 1997.*

Connelly et al., "Complete Short–Term Correction of Canine Hemophilia A by In Vivo Gene Therapy," *Blood* 88(10):3846–3853 (1996).
Connelly et al., "Sustained Phenotypic Correction of Murine Hemophilia A by In Vivo Gene Therapy," *Blood* 91(9):3273–3281 (May 1, 1998).
Lozier et al., "Gene Therapy and the Hemophilias," *JAMA* 271(1):47–51 (1994).
Snyder et al., "Persistent and Therapeutic Concentrations of Human Factor IX in Mice after Hepatic Gene Transfer of Recombinant AAV Vectors," *Nature Genetics* 16:270–276 (Jul. 1997).
Zatloukal et al., "In vivo production of human factor VIII in mice after intrasplenic implantation of primary fibroblasts transfected by receptor–mediated, adenovirus–augmented gene delivery," *Proc. Natl. Acad. Sci. USA* 91:5148–5152 (1994).

* cited by examiner

*Primary Examiner*—Deborah J.R. Clark
*Assistant Examiner*—David Nikdem
(74) *Attorney, Agent, or Firm*—Medlen & Carroll, LLP

(57) ABSTRACT

The present invention provides improved viral vectors useful for the expression of genes at high levels in human cells. In particular, the present invention provides recombinant adeno-associated vectors (AAV) suitable for gene therapy. These vectors are capable of delivering nucleic acid containing constructs which result in the production of full-length therapeutic levels of biologically active Factor VIII in the recipient individual in vivo. The present invention also provides pharmaceutical compositions comprising such AAV vectors, as well as methods for making and using these constructs.

25 Claims, 16 Drawing Sheets

| FIG. 5A |
|---|
| FIG. 5B |
| FIG. 5C |
| FIG. 5D |

FIG. 5

CAGCTGCGCGCTCGCTCGCTCACTGAGGCCGCCCGGGCAAAGCCCGGGCGTCGGGCGACCTTTGGTCGCCCGGCCTCAGT
GAGCGAGCGAGCGCGCAGAGAGGGAGTGGCCAACTCCATCACTAGGGGTTCCTGCGGCCGCCCAGGGAATGTTTGTTCTT
AAATACCATCCAGGGAATGTTTGTTCTTAAATACCATCCAGGGAATGTTTGTTCTTAAATACCATCTACAGTTATTGGTT
AAAGAAGTATATTAGAGCGAGTCTTTCTGCACACAGATCACCTTTCCGGGTGCCGCCCCTAGGCAGGTAAGTGCCGTGTG
TGGTTCCCGCGGGCCTGGCCTCTTTACGGGTTATGGCCCTTGCGTGCCTTGAATTACTGACACTGACATCCACTTTTTCT
TTTTCTCCACAGGTATCGATTCCACCATGCAAATAGAGCTCTCCACCTGCTTCTTTCTGTGCCTTTTGCGATTCTGCTTT
AGTGCCACCAGAAGATACTACCTGGGTGCAGTGGAACTGTCATGGGACTATATGCAAAGTGATCTCGGTGAGCTGCCTGT
GGACGCAAGATTTCCTCCTAGAGTGCCAAAATCTTTTCCATTCAACACCTCAGTCGTGTACAAAAAGACTCTGTTTGTAG
AATTCACGGATCACCTTTTCAACATCGCTAAGCCAAGGCCACCCTGGATGGGTCTGCTAGGTCCTACCATCCAGGCTGAG
GTTTATGATACAGTGGTCATTACACTTAAGAACATGGCTTCCCATCCTGTCAGTCTTCATGCTGTTGGTGTATCCTACTG
GAAAGCTTCTGAGGGAGCTGAATATGATGATCAGACCAGTCAAAGGGAGAAAGAAGATGATAAAGTCTTCCCTGGTGGAA
GCCATACATATGTCTGGCAGGTCCTGAAAGAGAATGGTCCAATGGCCTCTGACCCACTGTGCCTTACCTACTCATATCTT
TCTCATGTGGACCTGGTAAAAGACTTGAATTCAGGCCTCATTGGAGCCCTACTAGTATGTAGAGAAGGGAGTCTGGCCAA
GGAAAAGACACAGACCTTGCACAAATTTATACTACTTTTTGCTGTATTTGATGAAGGGAAAAGTTGGCACTCAGAAACAA
AGAACTCCTTGATGCAGGATAGGGATGCTGCATCTGCTCGGGCCTGGCCTAAAATGCACACAGTCAATGGTTATGTAAAC
AGGTCTCTGCCAGGTCTGATTGGATGCCACAGGAAATCAGTCTATTGGCATGTGATTGGAATGGGCACCACTCCTGAAGT
GCACTCAATATTCCTCGAAGGTCACACATTTCTTGTGAGGAACCATCGCCAGGCGTCCTTGGAAATCTCGCCAATAACTT
TCCTTACTGCTCAAACACTCTTGATGGACCTTGGACAGTTTCTACTGTTTTGTCATATCTCTTCCCACCAACATGATGGC
ATGGAAGCTTATGTCAAAGTAGACAGCTGTCCAGAGGAACCCCAACTACGAATGAAAAATAATGAAGAAGCGGAAGACTA
TGATGATGATCTTACTGATTCTGAAATGGATGTGGTCAGGTTTGATGATGACAACTCTCCTTCCTTTATCCAAATTCGCT
CAGTTGCCAAGAAGCATCCTAAAACTTGGGTACATTACATTGCTGCTGAAGAGGAGGACTGGGACTATGCTCCCTTAGTC
CTCGCCCCCGATGACAGAAGTTATAAAAGTCAATATTTGAACAATGGCCCTCAGCGGATTGGTAGGAAGTACAAAAAAGT
CCGATTTATGGCATACACAGATGAAACCTTTAAGACTCGTGAAGCTATTCAGCATGAATCAGGAATCTTGGGACCTTTAC
TTTATGGGGAAGTTGGAGACACACTGTTGATTATATTTAAGAATCAAGCAAGCAGACCATATAACATCTACCCTCACGGA
ATCACTGATGTCCGTCCTTTGTATTCAAGGAGATTACCAAAAGGTGTAAAACATTTGAAGGATTTTCCAATTCTGCCAGG
AGAAATATTCAAATATAAATGGACAGTGACTGTAGAAGATGGGCCAACTAAATCAGATCCTCGGTGCCTGACCCGCTATT
ACTCTAGTTTCGTTAATATGGAGAGAGATCTAGCTTCAGGACTCATTGGCCCTCTCCTCATCTGCTACAAAGAATCTGTA
GATCAAAGAGGAAACCAGATAATGTCAGACAAGAGGAATGTCATCCTGTTTTCTGTATTTGATGAGAACCGAAGCTGGTA
CCTCACAGAGAATATACAACGCTTTCTCCCCAATCCAGCTGGAGTGCAGCTTGAGGATCCAGAGTTCCAAGCCTCCAACA
TCATGCACAGCATCAATGGCTATGTTTTTGATAGTTTGCAGTTGTCAGTTTGTTTGCATGAGGTGGCATACTGGTACATT
CTAAGCATTGGAGCACAGACTGACTTCCTTTCTGTCTTCTTCTCTGGATATACCTTCAAACACAAAATGGTCTATGAAGA

FIG. 5A

```
CACACTCACCCTATTCCCATTCTCAGGAGAAACTGTCTTCATGTCGATGGAAAACCCAGGTCTATGGATTCTGGGGTGCC
ACAACTCAGACTTTCGGAACAGAGGCATGACCGCCTTACTGAAGGTTTCTAGTTGTGACAAGAACACTGGTGATTATTAC
GAGGACAGTTATGAAGATATTTCAGCATACTTGCTGAGTAAAAACAATGCCATTGAACCAAGAAGCTTCGAAATAACTCG
TACTACTCTTCAGTCAGATCAAGAGGAAATTGACTATGATGATACCATATCAGTTGAAATGAAGAAGGAAGATTTTGACA
TTTATGATGAGGATGAAAATCAGAGCCCCCGCAGCTTTCAAAAGAAAACACGACACTATTTTATTGCTGCAGTGGAGAGG
CTCTGGGATTATGGGATGAGTAGCTCCCCACATGTTCTAAGAAACAGGGCTCAGAGTGGCAGTGTCCCTCAGTTCAAGAA
AGTTGTTTTCCAGGAATTTACTGATGGCTCCTTTACTCAGCCCTTATACCGTGGAGAACTAAATGAACATTTGGGACTCC
TGGGGCCATATATAAGAGCAGAAGTTGAAGATAATATCATGGTAACTTTCAGAAATCAGGCCTCTCGTCCCTATTCCTTC
TATTCTAGCCTTATTTCTTATGAGGAAGATCAGAGGCAAGGAGCAGAACCTAGAAAAAACTTTGTCAAGCCTAATGAAAC
CAAAACTTACTTTTGGAAAGTGCAACATCATATGGCACCCACTAAAGATGAGTTTGACTGCAAAGCCTGGGCTTATTTCT
CTGATGTTGACCTGGAAAAAGATGTGCACTCAGGCCTGATTGGACCCCTTCTGGTCTGCCACACTAACACACTGAACCCT
GCTCATGGGAGACAAGTGACAGTACAGGAATTTGCTCTGTTTTTCACCATCTTTGATGAGACCAAAAGCTGGTACTTCAC
TGAAAATATGGAAAGAAACTGCAGGGCTCCCTGCAATATCCAGATGGAAGATCCCACTTTTAAAGAGAATTATCGCTTCC
ATGCAATCAATGGCTACATAATGGATACACTACCTGGCTTAGTAATGGCTCAGGATCAAAGGATTCGATGGTATCTGCTC
AGCATGGGCAGCAATGAAAACATCCATTCTATTCATTTCAGTGGACATGTGTTCACTGTACGAAAAAAAGAGGAGTATAA
AATGGCACTGTACAATCTCTATCCAGGTGTTTTTGAGACAGTGGAAATGTTACCATCCAAAGCTGGAATTTGGCGGGTGG
AATGCCTTATTGGCGAGCATCTACATGCTGGGATGAGCACACTTTTTCTGGTGTACAGCAATAAGTGTCAGACTCCCCTG
GGAATGGCTTCTGGACACATTAGAGATTTTCAGATTACAGCTTCAGGACAATATGGACAGTGGGCCCCAAAGCTGGCCAG
ACTTCATTATTCCGGATCAATCAATGCCTGGAGCACCAAGGAGCCCTTTTCTTGGATCAAGGTGGATCTGTTGGCACCAA
TGATTATTCACGGCATCAAGACCCAGGGTGCCCGTCAGAAGTTCTCCAGCCTCTACATCTCTCAGTTTATCATCATGTAT
AGTCTTGATGGGAAGAAGTGGCAGACTTATCGAGGAAATTCCACTGGAACCTTAATGGTCTTCTTTGGCAATGTGGATTC
ATCTGGGATAAAACACAATATTTTTAACCCTCCAATTATTGCTCGATACATCCGTTTGCACCCAACTCATTATAGCATTC
GCAGCACTCTTCGCATGGAGTTGATGGGCTGTGATTTAAATAGTTGCAGCATGCCATTGGGAATGGAGAGTAAAGCAATA
TCAGATGCACAGATTACTGCTTCATCCTACTTTACCAATATGTTTGCCACCTGGTCTCCTTCAAAAGCTCGACTTCACCT
CCAAGGGAGGAGTAATGCCTGGAGACCTCAGGTGAATAATCCAAAAGAGTGGCTGCAAGTGGACTTCCAGAAGACAATGA
AAGTCACAGGAGTAACTACTCAGGGAGTAAAATCTCTGCTTACCAGCATGTATGTGAAGGAGTTCCTCATCTCCAGCAGT
CAAGATGGCCATCAGTGGACTCTCTTTTTTCAGAATGGCAAAGTAAAGGTTTTTCAGGGAAATCAAGACTCCTTCACACC
TGTGGTGAACTCTCTAGACCCACCGTTACTGACTCGCTACCTTCGAATTCACCCCCAGAGTTGGGTGCACCAGATTGCCC
TGAGGATGGAGGTTCTGGGCTGCGAGGCACAGGACCTCTACTGACTCGAGAATAAAAGATCAGAGCTCTAGAGATCTGTG
TGTTGGTTTTTTGTGTGCGGCCGCAGGAACCCCTAGTGATGGAGTTGGCCACTCCCTCTCTGCGCGCTCGCTCGCTCACT
GAGGCCGGGCGACCAAAGGTCGCCCGACGCCCGGGCTTTGCCCGGGCGGCCTCAGTGAGCGAGCGAGCGCGCAGCTGCCT
GCAGGACATGTGAGCAAAAGGCCAGCAAAAGGCCAGGAACCGTAAAAAGGCCGCGTTGCTGGCGTTTTTCCATAGGCTCC
GCCCCCCTGACGAGCATCACAAAAATCGACGCTCAAGTCAGAGGTGGCGAAACCCGACAGGACTATAAAGATACCAGGCG
TTTCCCCCTGGAAGCTCCCTCGTGCGCTCTCCTGTTCCGACCCTGCCGCTTACCGGATACCTGTCCGCCTTTCTCCCTTC
GGGAAGCGTGGCGCTTTCTCATAGCTCACGCTGTAGGTATCTCAGTTCGGTGTAGGTCGTTCGCTCCAAGCTGGGCTGTG
TGCACGAACCCCCCGTTCAGCCCGACCGCTGCGCCTTATCCGGTAACTATCGTCTTGAGTCCAACCCGGTAAGACACGAC
TTATCGCCACTGGCAGCAGCCACTGGTAACAGGATTAGCAGAGCGAGGTATGTAGGCGGTGCTACAGAGTTCTTGAAGTG
GTGGCCTAACTACGGCTACACTAGAAGGACAGTATTTGGTATCTGCGCTCTGCTGAAGCCAGTTACCTTCGGAAAAAGAG
TTGGTAGCTCTTGATCCGGCAAACAAACCACCGCTGGTAGCGGTGGTTTTTTTGTTTGCAAGCAGCAGATTACGCGCAGA
AAAAAAGGATCTCAAGAAGATCCTTTGATCTTTTCTACGGGGTCTGACGCTCAGTGGAACGAAAACTCACGTTAAGGGAT
```

FIG. 5B

```
TTTGGTCATGAGATTATCAAAAAGGATCTTCACCTAGATCCTTTTAAATTAAAAATGAAGTTTTAAATCAATCTAAAGTA
TATATGAGTAAACTTGGTCTGACAGTTACCAATGCTTAATCAGTGAGGCACCTATCTCAGCGATCTGTCTATTTCGTTCA
TCCATAGTTGCCTGACTCCCCGTCGTGTAGATAACTACGATACGGGAGGGCTTACCATCTGGCCCCAGTGCTGCAATGAT
ACCGCGAGACCCACGCTCACCGGCTCCAGATTTATCAGCAATAAACCAGCCAGCCGGAAGGGCCGAGCGCAGAAGTGGTC
CTGCAACTTTATCCGCCTCCATCCAGTCTATTAATTGTTGCCGGGAAGCTAGAGTAAGTAGTTCGCCAGTTAATAGTTTG
CGCAACGTTGTTGCCATTGCTACAGGCATCGTGGTGTCACGCTCGTCGTTTGGTATGGCTTCATTCAGCTCCGGTTCCCA
ACGATCAAGGCGAGTTACATGATCCCCCATGTTGTGCAAAAAAGCGGTTAGCTCCTTCGGTCCTCCGATCGTTGTCAGAA
GTAAGTTGGCCGCAGTGTTATCACTCATGGTTATGGCAGCACTGCATAATTCTCTTACTGTCATGCCATCCGTAAGATGC
TTTTCTGTGACTGGTGAGTACTCAACCAAGTCATTCTGAGAATAGTGTATGCGGCGACCGAGTTGCTCTTGCCCGGCGTC
AATACGGGATAATACCGCGCCACATAGCAGAACTTTAAAAGTGCTCATCATTGGAAAACGTTCTTCGGGGCGAAAACTCT
CAAGGATCTTACCGCTGTTGAGATCCAGTTCGATGTAACCCACTCGTGCACCCAACTGATCTTCAGCATCTTTTACTTTC
ACCAGCGTTTCTGGGTGAGCAAAAACAGGAAGGCAAAATGCCGCAAAAAAGGGAATAAGGGCGACACGGAAATGTTGAAT
ACTCATACTCTTCCTTTTTCAATATTATTGAAGCATTTATCAGGGTTATTGTCTCATGAGCGGATACATATTTGAATGTA
TTTAGAAAAATAAACAAATAGGGGTTCCGCGCACATTTCCCCGAAAAGTGCCACCTGACGTCTAAGAAACCATTATTATC
ATGACATTAACCTATAAAAATAGGCGTATCACGAGGCCCTTTCGTCTCGCGCGTTTCGGTGATGACGGTGAAAACCTCTG
ACACATGCAGCTCCCGGAGACGGTCACAGCTTGTCTGTAAGCGGATGCCGGGAGCAGACAAGCCCGTCAGGGCGCGTCAG
CGGGTGTTGGCGGGTGTCGGGGCTGGCTTAACTATGCGGCATCAGAGCAGATTGTACTGAGAGTGCACCATAAAATTGTA
AACGTTAATATTTTGTTAAAATTCGCGTTAAATTTTTGTTAAATCAGCTCATTTTTTAACCAATAGGCCGAAATCGGCAA
AATCCCTTATAAATCAAAAGAATAGCCCGAGATAGGGTTGAGTGTTGTTCCAGTTTGGAACAAGAGTCCACTATTAAAGA
ACGTGGACTCCAACGTCAAAGGGCGAAAAACCGTCTATCAGGGCGATGGCCCACTACGTGAACCATCACCCAAATCAAGT
TTTTTGGGGTCGAGGTGCCGTAAAGCACTAAATCGGAACCCTAAAGGGAGCCCCCGATTTAGAGCTTGACGGGGAAAGCC
GGCGAACGTGGCGAGAAAGGAAGGGAAGAAAGCGAAAGGAGCGGGCGCTAGGGCGCTGGCAAGTGTAGCGGTCACGCTGC
GCGTAACCACCACACCCGCCGCGCTTAATGCGCCGCTACAGGGCGCGTACTATGGTTGCTTTGACGTATGCGGTGTGAAA
TACCGCACAGATGCGTAAGGAGAAAATACCGCATCAGGCCGTAACCTGTCGGATCACCGGAAAGGACCCGTAAAGTGATA
ATGATTATCATCTACATATCACAACGTGCGTGGAGGCCATCAAACCACGTCAAATAATCAATTATGACGCAGGTATCGTA
TTAATTGATCTGCATCAACTTAACGTAAAAACAACTTCAGACAATACAAATCAGCGACACTGAATACGGGCAACCTCAT
GTCAACGAAGAACAGAACCCGCAGAACAACAACCCGCAACATCCGCTTTCCTAACCAAATGATTGAACAAATTAACATCG
CTCTTGAGCAAAAAGGGTCCGGGAATTTCTCAGCCTGGGTCATTGAAGCCTGCCGTCGGAGACTAACGTCAGAAAAGAGA
GCATATACATCAATTAAAAGTGATGAAGAATGAACATCCCGCGTTCTTCCCTCCGAACAGGACGATATTGTAAATTCACT
TAATTACGAGGGCATTGCAGTAATTGAGTTGCAGTTTTACCACTTTCCTGACAGTGACAGACTGCGTGTTGGCTCTGTCA
CAGACTAAATAGTTTGAATGATTAGCAGTTATGGTGATCAGTCAACCACCAGGGAATAATCCTTCATATTATTATCGTGC
TTCACCAACGCTGCCTCAATTGCTCTGAATGCTTCCAGAGACACCTTATGTTCTATACATGCAATTACAACATCAGGGTA
ACTCATAGAAATGGTGCTATTAAGCATATTTTTTACACGAATCAGATCCACGGAGGGATCATCAGCAGATTGTTCTTTAT
TCATTTTGTCGCTCCATGCGCTTGCTCTTCATCTAGCGGTTAAAATATTACTTCAAATCTTTCTGTATGAAGATTTGAGC
ACGTTGGCCTTACATACATCTGTCGGTTGTATTTCCCTCCAGAATGCCAGCAGGACCGCACTTTGTTACGCAACCAATAC
TATTAAGTGAAAACATTCCTAATATTTGACATAAATCATCAACAAAACACAAGGAGGTCAGACCAGATTGAAACGATAAA
AACGATAATGCAAACTACGCGCCCTCGTATCACATGGAAGGTTTTACCAATGGCTCAGGTTGCCATTTTTAAAGAAATAT
TCGATCAAGTGCGAAAAGATTTAGACTGTGAATTGTTTTATTCTGAACTAAAACGTCACAACGTCTCACATTATATTTAC
TATCTAGCCACAGATAATATTCACATCGTGTTAGAAAACGATAACACCGTGTTAATAAAAGGACTTAAAAAGGTTGTAAA
TGTTAAATTCTCAAGAAACACGCATCTTATAGAAACGTCCTATGATAGGTTGAAATCAAGAGAAATCACATTTCAGCAAT
ACAGGGAAAATCTTGCTAAAGCAGGAGTTTTCCGATGGGTTACAAATATCCATGAACATAAAAGATATTACTATACCTTT
```

FIG. 5C

```
GATAATTCATTACTATTTACTGAGAGCATTCAGAACACTACACAAATCTTTCCACGCTAAATCATAACGTCCGGTTTCTT
CCGTGTCAGCACCGGGGCGTTGGCATAATGCAATACGTGTACGCGCTAAACCCTGTGTGCATCGTTTTAATTATTCCCGG
ACACTCCCGCAGAGAAGTTCCCCGTCAGGGCTGTGGACATAGTTAATCCGGGAATACAATGACGATTCATCGCACCTGAC
ATACATTAATAAATATTAACAATATGAAATTTCAACTCATTGTTTAGGGTTTGTTTAATTTTCTACACATACGATTCTGC
GAACTTCAAAAAGCATCGGGAATAACACCATGAAAAAAATGCTACTCGCTACTGCGCTGGCCCTGCTTATTACAGGATGT
GCTCAACAGACGTTTACTGTTCAAAACAAACCGGCAGCAGTAGCACCAAAGGAAACCATCACCCATCATTTCTTCGTTTC
TGGAATTGGGCAGAAGAAAACTGTCGATGCAGCCAAAATTTGTGGCGGCGCAGAAAATGTTGTTAAAACAGAAACCCAGC
AAACATTCGTAAATGGATTGCTCGGTTTTATTACTTTAGGCATTTATACTCCGCTGGAAGCGCGTGTGTATTGCTCACAA
TAATTGCATGAGTTGCCCATCGCGATATGGGCAACTCTATCTGCACTGCTCATTAATATACTTCTGGGTTCCTTCCAGTT
GTTTTTGCATAGTGATCAGCCTCTCTCTGAGGGTGAAATAATCCCGTTCAGCGGTGTCTGCCAGTCGGGGGGAGGCTGCA
TTATCCACGCCGGAGGCGGTGGTGGCTTCACGCACTGACTGACAGACTGCTTTGATGTGCAACCGACGACGACCAGCGGC
AACATCATCACGCAGAGCATCATTTTCAGCTTTAGCATCAGCTAACTCCTTCGTGTATTTTGCATCGAGCGCAGCAACAT
CACGCTGACGCATCTGCATGTCAGTAATTGCCGCGTTCGCCAGCTTCAGTTCTCTGGCATTTTTGTCGCGCTGGGCTTTG
TAGGTAATGGCGTTATCACGGTAATGATTAACAGCCCATGACAGGCAGACGATGATGCAGATAACCAGAGCGGAGATAAT
CGCGGTGACTCTGCTCATACATCAATCTCTCTGACCGTTCCGCCCGCTTCTTTGAATTTTGCAATCAGGCTGTCAGCCTT
ATGCTCGAACTGACCATAACCAGCGCCCGGCAGTGAAGCCCAGATATTGCTGCAACGGTCGATTGCCTGACGGATATCAC
CACGATCAATCATAGGTAAAGCGCCACGCTCCTTAATCTGCTGCAATGCCACAGCGTCCTGACTTTTCGGAGAGAAGTCT
TTCAGGCCAAGCTGCTTGCGGTAGGCATCCCACCAACGGGAAAGAAGCTGGTAGCGTCCGGCGCCTGTTGATTTGAGTTT
TGGGTTTAGCGTGACAAGTTTGCGAGGGTGATCGGAGTAATCAGTAAATAGCTCTCCGCCTACAATGACGTCATAACCAT
GATTTCTGGTTTTCTGACGTCCGTTATCAGTTCCCTCCGACCACGCCAGCATATCGAGGAACGCCTTACGTTGATTATTG
ATTTCTACCATCTTCTACTCCGGCTTTTTTAGCAGCGAAGCGTTTGATAAGCGAACCAATCGAGTCAGTACCGATGTAGC
CGATAAACACGCTCGTTATATAAGCGAGATTGCTACTTAGTCCGGCGAAGTCGAGAAGGTCACGAATGAACCAGGCGATA
ATGGCGCACATCGTTGCGTCGATTACTGTTTTTGTAAACGCACCGCCATTATATCTGCCGCGAAGGTACGCCATTGCAAA
CGCAAGGATTGCCCCGATGCCTTGTTCCTTTGCCGCGAGAATGGCGGCCAACAGGTCATGTTTTTCTGGCATCTTCATGT
CTTACCCCCAATAAGGGGATTTGCTCTATTTAATTAGGAATAAGGTCGATTACTGATAGAACAAATCCAGGCTACTGTGT
TTAGTAATCAGATTTGTTCGTGACCGATATGCACGGGCAAAACGGCAGGAGGTTGTTAGCGCGACCTCCTGCCACCCGCT
TTCACGAAGGTCATGTGTAAAAGGCCGCAGCGTAACTATTACTAATGAATTCAGGACAGACAGTGGCTACGGCTCAGTTT
GGGTTGTGCTGTTGCTGGGCGGCGATGACGCCTGTACGCATTTGGTGATCCGGTTCTGCTTCCGGTATTCGCTTAATTCA
GCACAACGGAAAGAGCACTGGCTAACCAGGCTCGCCGACTCTTCACGATTATCGACTCAATGCTCTTACCTGTTGTGCAG
ATATAAAAAATCCCGAAACCGTTATGCAGGCTCTAACTATTACCTGCGAACTGTTTCGGGATTGCATTTTGCAGACCTCT
CTGCCTGCGATGGTTGGAGTTCCAGACGATACGTCGAAGTGACCAACTAGGCGGAATCGGTAGTAAGCGCCGCCTCTTTT
CATCTCACTACCACAACGAGCGAATTAACCCATCGTTGAGTCAAATTTACCCAATTTTATTCAATAAGTCAATATCATGC
CGTTAATATGTTGCCATCCGTGGCAATCATGCTGCTAACGTGTGACCGCATTCAAAATGTTGTCTGCGATTGACTCTTCT
TTGTGGCATTGCACCACCAGAGCGTCATACAGCGGCTTAACAGTGCGTGACCAGGTGGGTTGGGTAAGGTTTGGGATTAG
CATCGTCACAGCGCGATATGCTGCGCTTGCTGGCATCCTTGAATAGCCGACGCCTTTGCATCTTCCGCACTCTTTCTCGA
CAACTCTCCCCCACAGCTCTGTTTTGGCAATATCAACCGCACGGCCTGTACCATGGCAATCTCTGCATCTTGCCCCCGGC
GTCGCGGCACTACGGCAATAATCCGCATAAGCGAATGTTGCGAGCACTTGCAGTACCTTTGCCTTAGTATTTCCTTCAAG
CTGCCCCTGCAGG
```

CGCCCCTGCAGGCAGCTGCGCGCTCGCTCGCTCACTGAGGCCGCCCGGGCAA
AGCCCGGGCGTCGGGCGACCTTTGGTCGCCCGGCCTCAGTGAGCGAGCGAGC
GCGCAGAGAGGGAGTGGCCAACTCCATCACTAGGGGTTCCTGCGGCCGCACG
CGTGGTGGCGCGGGTAAACTGGGAAAGTGATGTCGTGTACTGGCTCCGCCT
TTTTCCCGAGGGTGGGGGAGAACCGTATATAAGTGCAGTAGTCGCCGTGAAC
GTTCTTTTTCGCAACGGGTTTGCCGCCCCGCGGCAGGTAAGTGCCAGGGAAT
GTTTGTTCTTAAATACCATCGCTCCAGGGAATGTTTGTTCTTAAATACCATC
TACTGACACTGACATCCACTTTTTCTTTTTCTCCACAGGTATCGATCCACCA
TGCAAATAGAGCTCTCCACCTGCTTCTTTCTGTGCCTTTTGCGATTCTGCTT
TAGTGCCACCAGAAGATACTACCTGGGTGCAGTGGAACTGTCATGGGACTAT
ATGCAAAGTGATCTCGGTGAGCTGCCTGTGGACGCAAGATTTCCTCCTAGAG
TGCCAAAATCTTTTCCATTCAACACCTCAGTCGTGTACAAAAGACTCTGTT
TGTAGAATTCACGGATCACCTTTTCAACATCGCTAAGCCAAGGCCACCCTGG
ATGGGTCTGCTAGGTCCTACCATCCAGGCTGAGGTTTATGATACAGTGGTCA
TTACACTTAAGAACATGGCTTCCATCCTGTCAGTCTTCATGCTGTTGGTGT
ATCCTACTGGAAAGCTTCTGAGGGAGCTGAATATGATGATCAGACCAGTCAA
AGGGAGAAAGAAGATGATAAAGTCTTCCCTGGTGGAAGCCATACATATGTCT
GGCAGGTCCTGAAAGAGAATGGTCCAATGGCCTCTGACCCACTGTGCCTTAC
CTACTCATATCTTTCTCATGTGGACCTGGTAAAAGACTTGAATTCAGGCCTC
ATTGGAGCCCTACTAGTATGTAGAGAAGGGAGTCTGGCCAAGGAAAAGACAC
AGACCTTGCACAAATTTATACTACTTTTTGCTGTATTTGATGAAGGGAAAAG
TTGGCACTCAGAAACAAAGAACTCCTTGATGCAGGATAGGGATGCTGCATCT
GCTCGGGCCTGGCCTAAAATGCACACAGTCAATGGTTATGTAAACAGGTCTC
TGCCAGGTCTGATTGGATGCCACAGGAAATCAGTCTATTGGCATGTGATTGG
AATGGGCACCACTCCTGAAGTGCACTCAATATTCCTCGAAGGTCACACATTT
CTTGTGAGGAACCATCGCCAGGCGTCCTTGGAAATCTCGCCAATAACTTTCC
TTACTGCTCAAACACTCTTGATGGACCTTGGACAGTTTCTACTGTTTTGTCA
TATCTCTTCCACCAACATGATGGCATGGAAGCTTATGTCAAAGTAGACAGC
TGTCCAGAGGAACCCCAACTACGAATGAAAATAATGAAGAAGCGGAAGACT
ATGATGATGATCTTACTGATTCTGAAATGGATGTGGTCAGGTTTGATGATGA
CAACTCTCCTTCCTTTATCCAAATTCGCTCAGTTGCCAAGAAGCATCCTAAA

FIG. 6A

```
ACTTGGGTACATTACATTGCTGCTGAAGAGGAGGACTGGGACTATGCTCCCT
TAGTCCTCGCCCCCGATGACAGAAGTTATAAAAGTCAATATTTGAACAATGG
CCCTCAGCGGATTGGTAGGAAGTACAAAAAAGTCCGATTTATGGCATACACA
GATGAAACCTTTAAGACTCGTGAAGCTATTCAGCATGAATCAGGAATCTTGG
GACCTTTACTTTATGGGGAAGTTGGAGACACACTGTTGATTATATTTAAGAA
TCAAGCAAGCAGACCATATAACATCTACCCTCACGGAATCACTGATGTCCGT
CCTTTGTATTCAAGGAGATTACCAAAAGGTGTAAAACATTTGAAGGATTTTC
CAATTCTGCCAGGAGAAATATTCAAATATAAATGGACAGTGACTGTAGAAGA
TGGGCCAACTAAATCAGATCCTCGGTGCCTGACCCGCTATTACTCTAGTTTC
GTTAATATGGAGAGATCTAGCTTCAGGACTCATTGGCCCTCTCCTCATCT
GCTACAAGAATCTGTAGATCAAAGAGGAAACCAGATAATGTCAGACAAGAG
GAATGTCATCCTGTTTTCTGTATTTGATGAGAACCGAAGCTGGTACCTCACA
GAGAATATACAACGCTTTCTCCCCAATCCAGCTGGAGTGCAGCTTGAGGATC
CAGAGTTCCAAGCCTCCAACATCATGCACAGCATCAATGGCTATGTTTTTGA
TAGTTTGCAGTTGTCAGTTTGTTTGCATGAGGTGGCATACTGGTACATTCTA
AGCATTGGAGCACAGACTGACTTCCTTTCTGTCTTCTTCTCTGGATATACCT
TCAAACACAAAATGGTCTATGAAGACACACTCACCCTATTCCCATTCTCAGG
AGAAACTGTCTTCATGTCGATGGAAAACCCAGGTCTATGGATTCTGGGGTGC
CACAACTCAGACTTTCGGAACAGAGGCATGACCGCCTTACTGAAGGTTTCTA
GTTGTGACAAGAACACTGGTGATTATTACGAGGACAGTTATGAAGATATTTC
AGCATACTTGCTGAGTAAAAACAATGCCATTGAACCAAGAAGCTTCTCCCAG
AATCCACCAGTCTTGAAACGCCATCAACGCGAAATAACTCGTACTACTCTTC
AGTCAGATCAAGAGGAAATTGACTATGATGATACCATATCAGTTGAAATGAA
GAAGGAAGATTTTGACATTTATGATGAGGATGAAAATCAGAGCCCCCGCAGC
TTTCAAAAGAAAACACGACACTATTTTATTGCTGCAGTGGAGAGGCTCTGGG
ATTATGGGATGAGTAGCTCCCCACATGTTCTAAGAAACAGGGCTCAGAGTGG
CAGTGTCCCTCAGTTCAAGAAAGTTGTTTTCCAGGAATTTACTGATGGCTCC
TTTACTCAGCCCTTATACCGTGGAGAACTAAATGAACATTTGGGACTCCTGG
GGCCATATATAAGAGCAGAAGTTGAAGATAATATCATGGTAACTTTCAGAAA
TCAGGCCTCTCGTCCCTATTCCTTCTATTCTAGCCTTATTTCTTATGAGGAA
GATCAGAGGCAAGGAGCAGAACCTAGAAAAACTTTGTCAAGCCTAATGAAA
CCAAAACTTACTTTTGGAAAGTGCAACATCATATGGCACCCACTAAAGATGA
GTTTGACTGCAAAGCCTGGGCTTATTTCTCTGATGTTGACCTGGAAAAAGAT
GTGCACTCAGGCCTGATTGGACCCCTTCTGGTCTGCCACACTAACACACTGA
ACCCTGCTCATGGGAGACAAGTGACAGTACAGGAATTTGCTCTGTTTTCAC
CATCTTTGATGAGACCAAAAGCTGGTACTTCACTGAAAATATGGAAAGAAAC
TGCAGGGCTCCCTGCAATATCCAGATGGAAGATCCCACTTTTAAAGAGAATT
ATCGCTTCCATGCAATCAATGGCTACATAATGGATACACTACCTGGCTTAGT
AATGGCTCAGGATCAAAGGATTCGATGGTATCTGCTCAGCATGGGCAGCAAT
```

FIG. 6B

```
GAAAACATCCATTCTATTCATTTCAGTGGACATGTGTTCACTGTACGAAAAA
AAGAGGAGTATAAAATGGCACTGTACAATCTCTATCCAGGTGTTTTGAGAC
AGTGGAAATGTTACCATCCAAAGCTGGAATTTGGCGGGTGGAATGCCTTATT
GGCGAGCATCTACATGCTGGGATGAGCACACTTTTTCTGGTGTACAGCAATA
AGTGTCAGACTCCCTGGGAATGGCTTCTGGACACATTAGAGATTTTCAGAT
TACAGCTTCAGGACAATATGGACAGTGGGCCCCAAAGCTGGCCAGACTTCAT
TATTCCGGATCAATCAATGCCTGGAGCACCAAGGAGCCCTTTTCTTGGATCA
AGGTGGATCTGTTGGCACCAATGATTATTCACGGCATCAAGACCCAGGGTGC
CCGTCAGAAGTTCTCCAGCCTCTACATCTCTCAGTTTATCATCATGTATAGT
CTTGATGGGAAGAAGTGGCAGACTTATCGAGGAAATTCCACTGGAACCTTAA
TGGTCTTCTTTGGCAATGTGGATTCATCTGGGATAAAACACAATATTTTTAA
CCCTCCAATTATTGCTCGATACATCCGTTTGCACCCAACTCATTATAGCATT
CGCAGCACTCTTCGCATGGAGTTGATGGGCTGTGATTTAAATAGTTGCAGCA
TGCCATTGGGAATGGAGAGTAAAGCAATATCAGATGCACAGATTACTGCTTC
ATCCTACTTTACCAATATGTTTGCCACCTGGTCTCCTTCAAAAGCTCGACTT
CACCTCCAAGGGAGGAGTAATGCCTGGAGACCTCAGGTGAATAATCCAAAAG
AGTGGCTGCAAGTGGACTTCCAGAAGACAATGAAAGTCACAGGAGTAACTAC
TCAGGGAGTAAAATCTCTGCTTACCAGCATGTATGTGAAGGAGTTCCTCATC
TCCAGCAGTCAAGATGGCCATCAGTGGACTCTCTTTTTTCAGAATGGCAAAG
TAAAGGTTTTTCAGGGAAATCAAGACTCCTTCACACCTGTGGTGAACTCTCT
AGACCCACCGTTACTGACTCGCTACCTTCGAATTCACCCCAGAGTTGGGTG
CACCAGATTGCCCTGAGGATGGAGGTTCTGGGCTGCGAGGCACAGGACCTCT
ACTGACTCGAGCCTAATAAAGGAAATTTATTTTCATTGCAATAGTGTGTTGG
TTTTTTGTGTGCGGCCGCAGGAACCCCTAGTGATGGAGTTGGCCACTCCCTC
TCTGCGCGCTCGCTCGCTCACTGAGGCCGGGCGACCAAAGGTCGCCCGACGC
CCGGGCTTTGCCCGGGCGGCCTCAGTGAGCGAGCGAGCGCGCAGCTGCCTGC
AGGACAT
```

FIG. 6C

ADENO-ASSOCIATED VIRUS VECTORS FOR EXPRESSION OF FACTOR VIII BY TARGET CELLS

This application is a Continuation-in-Part of U.S. patent application Ser. No. 09/364,862, filed Jul. 30, 1999, which claims benefit of U.S. provisional application No. 60/125,974 filed Mar. 24, 1999 and No. 60/104,994 filed Oct. 20, 1998, all of which are hereby incorporated by reference in their entireties.

FIELD OF THE INVENTION

The present invention relates to AAV vectors suitable for hemophilia gene therapy. More particularly, these AAV vectors are suitable for delivering nucleic acids encoding Factor VIII into a recipient subject suffering from hemophilia A, such that the subject's blood is able to clot.

BACKGROUND

Hemophilia is a genetic disease characterized by a blood clotting deficiency. In hemophilia A (classic hemophilia, Factor VIII deficiency), an X-chromosome-linked genetic defect disrupts the gene encoding Factor VIII, a plasma glycoprotein, which is a key component in the blood clotting cascade. Human Factor VIII is synthesized as a single chain polypeptide, with a predicted molecular weight of 265 kDa. The Factor VIII gene codes for 2351 amino acids, and the protein has six domains, designated from the amino to the carboxy terminus as A1-A2-B-A3-C1-C2 (Wood et al., Nature 312:330 [1984]; Vehar et al., Nature 312:337 [1984]; and Toole et al., Nature 312:342 [1984]). Human Factor VIII is processed within the cell to yield a heterodimer primarily comprised of a heavy chain of 200 kDa containing the A1, A2, and B domains and an 80 kDa light chain containing the A3, C1, and C2 domains (Kaufman et al., J. Biol. Chem., 263:6352–6362 [1988]). Both the single chain polypeptide and the heterodimer circulate in the plasma as inactive precursors (Ganz et al., Eur. J. Biochem., 170:521–528 [1988]). Activation of Factor VIII in plasma is initiated by thrombin cleavage between the A2 and B domains, which releases the B domain and results in a heavy chain consisting of the A1 and A2 domains. The 980 amino acid B domain is deleted in the activated procoagulant form of the protein. Additionally, in the native protein, two polypeptide chains ("a" and "b"), flanking the B domain, are bound to a divalent calcium cation. Hemophilia may result from point mutations, deletions, or mutations resulting in a stop codon (See, Antonarakis et al., Mol. Biol. Med., 4:81 [1987]).

The disease is relatively rare, afflicting approximately one in 10,000 males. Hemophilia in females is extremely rare, although it may occur in female children of an affected father and carrier mother, as well as in females with X-chromosomal abnormalities (e.g., Turner syndrome, X mosaicism, etc.). The severity of each patient's disease is broadly characterized into three groups—"mild," "moderate," and "severe," depending on the severity of the patient's symptoms and circulating Factor VIII levels. While normal levels of Factor VIII range between 50 and 200 ng/mL plasma, mildly affected patients have 6–60% of this value, and moderately affected patients have 1–5% of this value. Severely affected hemophiliacs have less than 1% of normal Factor VIII levels.

While hemophiliacs clearly require clotting factor after surgery or severe trauma, on a daily basis, spontaneous internal bleeding is a greater concern. Hemophiliacs experience spontaneous hemorrhages from early infancy, as well as frequent spontaneous hemarthroses and other hemorrhages requiring clotting factor replacement. Without effective treatment, chronic hemophilic arthropathy occurs by young adulthood. Severely affected patients are prone to serious hemorrhages that may dissect through tissue planes, ultimately resulting in death due to compromised vital organs.

Hematomas are commonly observed in moderately and severely affected hemophiliacs. In these patients, hematomas have a tendency to progressively enlarge and dissect in all directions. Some of these hematomas expand locally, resulting in local compression of adjacent organs, blood vessels, and nerves. A rare, yet often fatal, complication of abdominal hematomas is the perforation and drainage of the hematoma into the colon, resulting in infection and septicemia. Intracranial and/or extracranial hemorrhage also represent very dangerous bleeding situations. While subcutaneous hematomas may dissect into muscle, pharyngeal and retropharyngeal hematomas (e.g., complicating bacterial or viral pharyngitis) may enlarge and obstruct the airway, sometimes resulting in a life-threatening situation that requires administration of a sufficient dose of Factor VIII concentrate to normalize the Factor VIII level.

In addition to hematomas, hemarthroses are commonly observed in hemophiliacs, with bleeding into the joint accounting for approximately 75% of hemophilic bleeding. Repeated hemorrhaging into the joints eventually results in extensive destruction of articular cartilage, synovial hyperplasia, and other reactive changes in adjacent tissues and bone. A major complication of repeated hemarthroses is joint deformity, which is often accompanied by muscle atrophy and soft tissue contractures; osteoporosis and cystic areas in the subchondral bone may also develop, along with progressive loss of joint space.

Other symptoms are often observed in hemophiliacs, including hematuria and mucous membrane bleeding. Hematuria is experienced by virtually all severely affected hemophiliacs sometime during their lifetimes, and mucous membrane bleeding is common in hemophiliacs. Bone cysts (pseudotumors) are rare, but dangerous complications of hemophilic bleeding. In many of these cases, immediate treatment is necessary.

In the early 1980s, many severely affected hemophiliacs were treated with Factor VIII concentrate about three times weekly. Unfortunately, these concentrates transmitted viruses, such as hepatitis B and/or C, and human immunodeficiency virus (HIV). In the United States and Western Europe, at least 75% of Factor VIII concentrate recipients have been reported to have anti-HIV antibodies (See, Schrier and Leung, "Disorders of Hemostasis and Coagulation, " in Dale Federman (eds), *Scientific American Medicine*, Scientific American, New York, pp. 36–57 (1996)). Some of these patients also developed HIV-associated immune thrombocytopenia, a very serious complication in hemophiliacs. In spite of antiviral therapy (e.g., with zidovudine and pentamidine prophylaxis), which has tended to slow disease progression, full-blown AIDS (acquired immunodeficiency syndrome) occurs at an inexorable rate in hemophiliacs infected with HIV. Indeed, this has reversed the improvement in the life expectancy of hemophiliacs, which peaked at 66 years of age during the 1970s, and has dropped to 49 years (See, Schrier and Leung, "Disorders of Hemostasis and Coagulation," in Dale and Federman (eds.), *Scientific American Medicine*, Scientific American, New York, pp. 36–57 (1996)). The development of virus-free preparations and recombinant Factor VIII has helped control infectious viral contamination.

However, for hemophiliacs, the availability of viral-free concentrates and recombinant Factor VIII, while significant, is but part of the solution. In order to prevent spontaneous internal bleeding episodes, patients suffering from hemophilia A must consistently have serum Factor VIII levels of about 1%, and preferably 5%. Currently, the cost of viral-free concentrates and recombinant Factor VIII make it prohibitively expensive to administer the clotting factor prophylactically or on a maintenance basis. Indeed, most hemophiliacs in the U.S. do not receive recombinant Factor VIII therapy on a maintenance basis, but only receive it prior to activities or events which might cause bleeding (e.g., surgery), or as a treatment for spontaneous bleeding.

Moreover, even if cost effective preparations of recombinant or virus-free Factor VIII were available, a steady state level of Factor VIII cannot be achieved by its daily administration. At best, patients receive widely varying levels of Factor VIII. Immediately following the administration, the levels are super-physiological, while prior to administration the levels are sub-physiological. Thus, there remains a need for methods and compositions that are relatively economic, yet effective in the treatment and prevention of bleeding in hemophiliacs, particularly spontaneous bleeds. Furthermore, there is a need in the art for methods and compositions for long term delivery of clotting factors (e.g., Factor VIII) which more closely mimic the steady state physiological levels observed in normal individuals.

SUMMARY OF THE INVENTION

The present invention provides improved viral vectors suitable for gene therapy to treat hemophilia. In particular, the present invention provides AAV vectors and methods for treating hemophilia A by delivering nucleic acids coding for the clotting protein Factor VIII. The present invention also provides pharmaceutical compositions comprising such AAV vectors, as well as methods for making and using the vectors.

The present invention is particularly suited for use in hemophilia A gene therapy. Accordingly, in one embodiment of the invention, at least one AAV vector containing a nucleic acid molecule encoding Factor VIII is operably linked to control sequences that direct expression of Factor VIII in a suitable recipient cell. The AAV vectors are then introduced into a recipient cell of the subject, under conditions that result in expression of Factor VIII. The subject, therefore, has a continuous supply of Factor VIII available to clot blood during bleeding episodes.

Using the methods of the present invention, long term expression of therapeutic levels of Factor VIII have been achieved in vivo. In one embodiment, animals were administered, via the portal vein, two AAV vectors: one carrying the DNA sequence coding for the heavy chain of Factor VIII and the other carrying the DNA sequence coding for the light chain of Factor VIII. Blood samples were collected periodically and assayed for Factor VIII activity. Reproducibly, animals expressed between 600 and 900 ng/ml of biologically active Factor VIII, levels that are well above the normal physiological levels of approximately 200 ng/ml. Furthermore, these levels have been sustained for over 13 months without a decrease in Factor VIII levels or activity. In a related embodiment, a B-domain deleted form of Factor VIII was cloned into a single AAV vector and shown to express biologically active Factor VIII.

It is not intended, however, that the present invention be limited to specific embodiments. Many different forms of recombinant Factor VIII have been made and tested both in vitro and in vivo, using a variety of different control and regulatory sequences. Any DNA sequence coding for biologically active Factor VIII can be expressed using the AAV vectors and methods taught in the present invention. Therefore, the present invention encompasses any AAV vector or vectors containing Factor VIII sequences that produce biologically active Factor VIII protein in vitro or in vivo.

For example, in some embodiments, the AAV vector contains the first 57 base pairs of the Factor VIII heavy chain which encodes the 10 amino acid signal sequence, as well as the human growth hormone (hGH) polyadenylation sequence. In some alternative embodiments, the vector also contains the A1 and A2 domains, as well as 5 amino acids from the N-terminus of the B domain, and/or 85 amino acids of the C-terminus of the B domain, as well as the A3, C1, and C2 domains. In yet other embodiments, the nucleic acids coding for Factor VIII heavy chain and light chain were cloned into a single vector separated by 42 nucleic acids coding for 14 amino acids of the B domain.

The present invention also provides methods for administering the above-described vectors. For example, it is intended that the present invention encompass methods suitable for delivery of the AAV vectors to the livers of recipient patients or test animals. It is not intended that the present invention be limited to any particular route of administration. However, in preferred embodiments, the AAV vectors of the present invention are successfully administered via the portal or arterial vasculature.

These and other embodiments of the invention will readily occur to those of ordinary skill in the art in view of the disclosure herein.

BRIEF DESCRIPTION OF THE DRAWINGS

FIG. 5 provides the sequence of pAAV-F8-1 (ITR to ITR), with the plasmid backbone omitted.

FIG. 6 provides the sequence of pVm4.1cF8ΔB (ITR to ITR), with the plasmid backbone omitted.

GENERAL DESCRIPTION OF THE INVENTION

Figure 1:
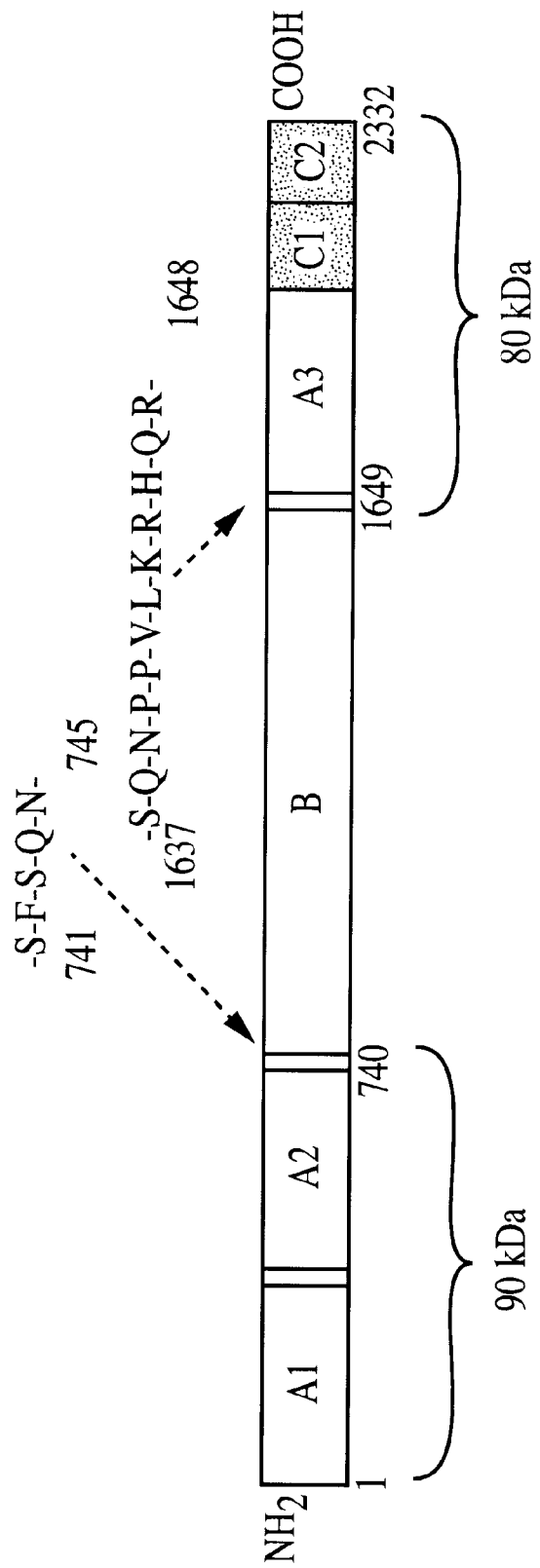
FIG. 1 provides a schematic representation of the Factor VIII protein.
Figure 2:
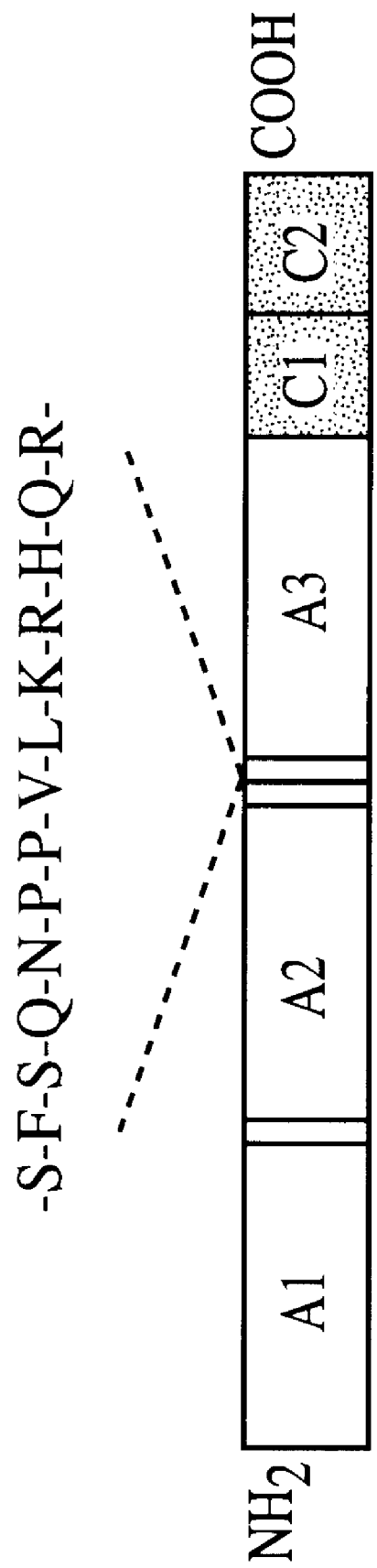
FIG. 2 provides a schematic representation of a B-domain deleted form of Factor VIII protein.
Figure 3:
FIG. 3 provides a schematic representation of a B-domain deleted Factor VIII AAV construct (AAV-F8-1) from internal terminal repeat (ITR to ITR), including control sequences.
Figure 4:
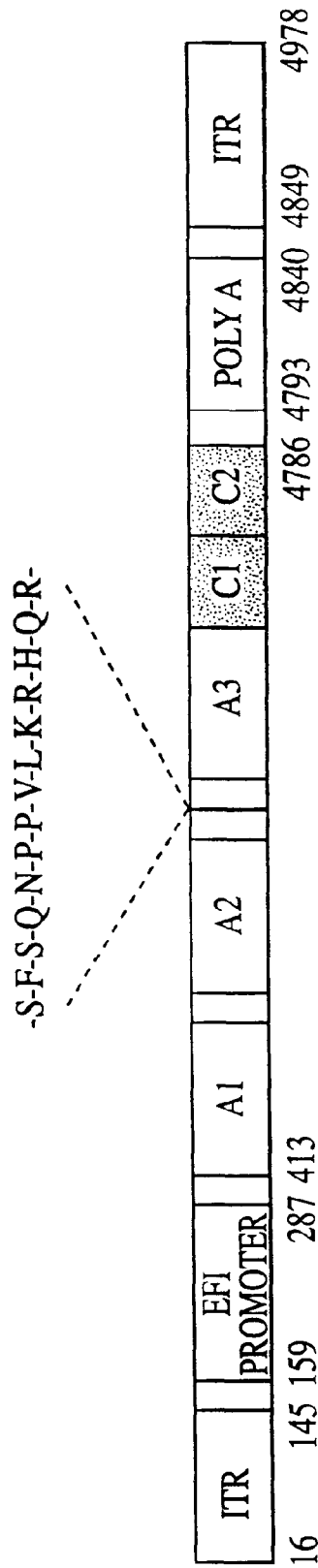
FIG. 4 provides a schematic representation of a B-domain deleted Factor VIII AAV construct (PVM4.1c-F8AB) from internal terminal repeat (ITR to ITR), including control sequences.

The present invention relates to improved viral vectors useful for expressing gene products at high levels in human cells. In particular, the present invention provides AAV vectors suitable for gene therapy. These vectors are capable of delivering nucleic acid containing constructs which result in the production of Factor VIII protein in a host. The present invention also provides pharmaceutical compositions comprising such AAV vectors, as well as methods for making and using the constructs.

The AAV vectors and rAAV virions of the present invention can be produced using standard methodology known to those of skill in the art. The methods generally involve the steps of: (1) introducing an AAV vector into a host cell; (2) introducing an AAV helper construct into the host cell, where the helper construct includes AAV coding regions capable of being expressed in the host cell to complement AAV helper functions missing from the AAV vector; (3) introducing one or more helper viruses and/or accessory function vectors into the host cell, wherein the helper virus and/or accessory function vectors provide accessory functions capable of supporting efficient recombinant AAV ("rAAV") virion production in the host cell; and (4) culturing the host cell to produce rAAV virions. The AAV vector, AAV helper construct and the helper virus or accessory function vector(s) can be introduced into the host cell either simultaneously or serially, using standard transfection techniques.

Unless otherwise indicated, the practice of the present invention employs conventional methods of virology, microbiology, molecular biology and recombinant DNA techniques within the skill of the art, including those described in such references as Sambrook et al. (eds.) *Molecular Cloning: A Laboratory Manual;* Glover (ed.) *DNA Cloning: A Practical Approach,* Vols. I and II; Gait (ed.) *Oligonucleotide Synthesis;* Hames and Higgins (eds.) *Nucleic Acid Hybridization;* Hames and Higgins (eds.) *Transcription and Translation;* Tijessen (ed.) *CRC Handbook of Parvoviruses,* Vols. I and II; and Fields and Knipe (eds.) *Fundamental Virology,* 2nd Edition, Vols. I and II.

Definitions

In describing the present invention, the following terms will be employed, and are intended to be defined as indicated below.

As used herein, the terms "gene transfer" and "gene delivery" refer to methods or systems for reliably inserting a particular nucleotide sequence (e.g., DNA) into targeted cells. In particularly preferred embodiments, the nucleotide sequence comprises at least a portion of Factor VIII.

As used herein, the terms "vector," and "gene transfer vector" refer to any genetic element, such as a plasmid, phage, transposon, cosmid, chromosome, virus, virion, etc., which is capable of replication when associated with the proper control sequences and/or which can transfer nucleic acid sequences between cells. Thus, the term includes cloning and expression vectors, as well as viral vectors.

Gene transfer vectors may include transcription sequences such as polyadenylation sites, selectable markers or reporter genes, enhancer sequences, and other control sequences which allow for the induction of transcription. Such control sequences are described more fully below.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, as well as other sequences. Eukaryotic cells are generally known to utilize promoters (constitutive, inducible or tissue specific), enhancers, and termination and polyadenylation signals, although some elements may be deleted and other elements added without sacrificing the necessary expression.

As used herein, the terms "host" and "expression host" refer to organisms and/or cells which harbor an exogenous DNA sequence (e.g., via transfection), an expression vector or vehicle, as well as organisms and/or cells that are suitable for use in expressing a recombinant gene or protein. It is not intended that the present invention be limited to any particular type of cell or organism. Indeed, it is contemplated that any suitable organism and/or cell will find use in the present invention as a host.

As used herein, the terms "viral replicons" and "viral origins of replication" refer to viral DNA sequences that allow for the extrachromosomal replication of a vector in a host cell expressing the appropriate replication factors. In some embodiments, vectors which contain either the SV40 or polyoma virus origin of replication replicate to high copy number, while vectors which contain the replicons from bovine papillomavirus or Epstein-Barr virus replicate extrachromosomally at low copy number may be utilized in other embodiments.

As used herein, the term "AAV vector" refers to a vector having functional or partly functional ITR sequences. The ITR sequences may be derived from an adeno-associated virus serotype, including without limitation, AAV-1, AAV-2, AAV-3, AAV-4, AAV-5, AAV-X7, etc. The ITRs, however, need not be the wild-type nucleotide sequences, and may be altered (e.g., by the insertion, deletion or substitution of nucleotides), so long as the sequences retain function provide for functional rescue, replication and packaging. AAV vectors can have one or more of the AAV wild-type genes deleted in whole or part, preferably the rep and/or cap genes but retain functional flanking ITR sequences. Functional ITR sequences are necessary for the rescue, replication and packaging of the AAV virion. Thus, an "AAV vector" is defined herein to include at least those sequences required in cis for replication and packaging (e.g., functional ITRs) of the virus.

As used herein, the term "ITR" refers to inverted terminal repeats. The terms "adeno-associated virus inverted terminal repeats" or "AAV ITRs" refer to the art-recognized palindromic regions found at each end of the AAV genome which function together in cis as origins of DNA replication and as packaging signals for the virus. For use in some embodiments of the present invention, flanking AAV ITRs are positioned 5' and 3' of one or more selected heterologous nucleotide sequences. Optionally, the ITRs together with the rep coding region or the Rep expression product provide for the integration of the selected sequences into the genome of a target cell.

As used herein, the term "AAV rep coding region" refers to the art-recognized region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome. Muzyczka (Muzyczka, Curr. Top. Microbiol. Immunol., 158:97–129 [1992]) and Kotin (Kotin, Hum. Gene Ther., 5:793–801 [1994]) provide additional descriptions of the AAV rep coding region, as well as the cap coding region described below. Suitable homologues of the AAV rep coding region include the human herpesvirus 6 (HHV-6) rep gene which is also known to mediate AAV-2 DNA replication (Thomson el al., Virol., 204:304–311 [1994]).

As used herein, the term "AAV cap coding region" refers to the art-recognized region of the AAV genome which encodes the capsid proteins VP1, VP2, and VP3, or functional homologues thereof. These cap expression products supply the packaging functions which are collectively required for packaging the viral genome.

As used herein, the term "AAV helper function" refers to AAV coding regions capable of being expressed in the host cell to complement AAV viral functions missing from the AAV vector. Typically, the AAV helper functions include the AAV rep coding region and the AAV cap coding region. An "AAV helper construct" is a vector containing AAV coding regions required to complement AAV viral functions missing from the AAV vector (e.g., the AAV rep coding region and the AAV cap coding region).

As used herein, the terms "accessory functions" and "accessory factors" refer to functions and factors that are required by AAV for replication, but are not provided by the AAV virion (or rAAV virion) itself. Thus, these accessory functions and factors must be provided by the host cell, a virus (e.g., adenovirus or herpes simplex virus), or another expression vector that is co-expressed in the same cell. Generally, the E1, E2A, E4 and VA coding regions of adenovirus are used to supply the necessary accessory function required for AAV replication and packaging (Matsushita et al., Gene Therapy 5:938 [1998]).

As used herein, the term "wild type" ("wt") refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the term "AAV virion" refers to a complete virus particle, such as a "wild-type" (wt) AAV virus particle (comprising a linear, single-stranded AAV nucleic acid genome associated with an AAV capsid protein coat). In this regard, single-stranded AAV nucleic acid molecules of either complementary sense (e.g., "sense" or "antisense" strands), can be packaged into any one AAV virion and both strands are equally infectious.

As used herein, the terms "recombinant AAV virion," and "rAAV virion" refer to an infectious viral particle containing a heterologous DNA molecule of interest (e.g., Factor VIII sequence) which is flanked on both sides by AAV ITRs. In some embodiments of the present invention, an rAAV virion is produced in a suitable host cell which contains an AAV vector, AAV helper functions and accessory functions introduced therein. In this manner, the host cell is rendered capable of encoding AAV polypeptides that are required for packaging the AAV vector containing a recombinant nucleotide sequence of interest, such as at least a portion of Factor VIII or portions of Factor VIII domains, into recombinant virion particles for subsequent gene delivery.

As used herein, the term "transfection" refers to the uptake of foreign DNA by a cell, and a cell has been "transfected" when exogenous DNA has been introduced inside the cell membrane. A number of transfection techniques are generally known in the art (See e.g., Graham et al., Virol., 52:456 [1973]; Sambrook et al., Molecular Cloning, a Laboratory Manual, Cold Spring Harbor Laboratories, New York [1989]; Davis et al., Basic Methods in Molecular Biology, Elsevier, [1986]; and Chu et al., Gene 13:197 [1981]. Such techniques can be used to introduce one or more exogenous DNA moieties, such as a gene transfer vector and other nucleic acid molecules, into suitable recipient cells.

As used herein, the terms "stable transfection" and "stably transfected" refers to the introduction and integration of foreign DNA into the genome of the transfected cell. The term "stable transfectant" refers to a cell which has stably integrated foreign DNA into the genomic DNA.

As used herein, the term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells which have taken up foreign DNA but have failed to integrate this DNA.

As used herein, the term "transduction" denotes the delivery of a DNA molecule to a recipient cell either in vivo or in vitro, via a replication-defective viral vector, such as via a recombinant AAV virion.

As used herein, the term "recipient cell" refers to a cell which has been transfected or transduced, or is capable of being transfected or transduced, by a nucleic acid construct or vector bearing a selected nucleotide sequence of interest (i.e., Factor VIII). The term includes the progeny of the parent cell, whether or not the progeny are identical in morphology or in genetic make-up to the original parent, so long as the selected nucleotide sequence is present.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transfected with a construct which is not normally present in the cell would be considered heterologous for purposes of this invention. Allelic variation or naturally occurring mutational events do not give rise to heterologous DNA, as used herein.

As used herein, "coding sequence" or a sequence which "encodes" a particular antigen, is a nucleic acid sequence which is transcribed (in the case of DNA) and translated (in the case of mRNA) into a polypeptide in vitro or in vivo, when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the coding sequence.

As used herein, the term "nucleic acid" sequence refers to a DNA or RNA sequence. The term captures sequences that include any of the known base analogues of DNA and RNA such as, but not limited to 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "recombinant DNA molecule" as used herein refers to a DNA molecule which is comprised of segments of DNA joined together by means of molecular biological techniques.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc. (defined infra).

The term DNA "control sequences" refers collectively to regulatory elements such as promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate recipient cell.

Transcriptional control signals in eukaryotes generally comprise "promoter" and "enhancer" elements. Promoters and enhancers consist of short arrays of DNA sequences that interact specifically with cellular proteins involved in transcription (Maniatis et al., Science 236:1237 [1987]). Promoter and enhancer elements have been isolated from a variety of eukaryotic sources including genes in yeast, insect and mammalian cells and viruses (analogous control sequences, i.e., promoters, are also found in prokaryotes). The selection of a particular promoter and enhancer depends on what cell type is to be used to express the protein of interest (i.e., Factor VIII). Some eukaryotic promoters and enhancers have a broad host range while others are functional in a limited subset of cell types (See e.g., Voss et al., Trends Biochem. Sci., 11:287 [1986]; and Maniatis et al., supra, for reviews). For example, the SV40 early gene enhancer is very active in a wide variety of cell types from many mammalian species and has been widely used for the expression of proteins in mammalian cells (Dijkema et al, EMBO J. 4:761 [1985]). Two other examples of promoter and enhancer elements active in a broad range of mammalian cell types are those from the human elongation factor 1α gene (Uetsuki et al., J. Biol. Chem., 264:5791 [1989]; Kim et al., Gene 91:217 [1990]; and Mizushima and Nagata, Nucl. Acids. Res., 18:5322 [1990]) and the long terminal repeats of the Rous sarcoma virus (Gorman et al., Proc. Natl. Acad. Sci. U.S.A. 79:6777 [1982]) and the human cytomegalovirus (Boshart et al., Cell 41:521 [1985]). Promoters and enhances can be found naturally alone or together. For example, the long terminal repeats of retroviruses contain both promoter and enhancer functions Moreover, generally promoters and enhances act independently of the gene being transcribed or translated. Thus, the enhancer and promoter may be "endogenous" or "exogenous" or "heterologous." An "endogenous" enhancer/promoter is one which is naturally linked with a given gene in the genome. An "exogenous" or "heterologous" enhancer and promoter is one which is placed in juxtaposition to a gene by means of genetic manipulation (i.e., molecular biological techniques) such that transcription of that gene is directed by the linked enhancer/promoter.

As used herein, the term "tissue specific" refers to regulatory elements or control sequences, such as a promoter, enhancers, etc., wherein the expression of the nucleic acid sequence is substantially greater in a specific cell type(s) or tissue(s). In particularly preferred embodiments, the albumin promoter and the transthyretin promoter display increased expression of FVIII in hepatocytes, as compared to other cell types. It is not intended, however, that the present invention be limited to the albumin or transthyretin promoters or to hepatic-specific expression, as other tissue specific regulatory elements, or regulatory elements that display altered gene expression patterns, are contemplated.

The presence of "splicing signals" on an expression vector often results in higher levels of expression of the recombinant transcript. Splicing signals mediate the removal of introns from the primary RNA transcript and consist of a splice donor and acceptor site (Sambrook et al., *Molecular Cloning: A Laboratory Manual,* 2nd ed., Cold Spring Harbor Laboratory Press, New York [1989], pp. 16.7–16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is one which is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation (Sambrook et al., supra, at 16.6–16.7).

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is such present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs which encode a multitude of proteins. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein, the term "purified" or "to purify" refers to the removal of contaminants from a sample. For example, antibodies may be purified by removal of contaminating non-immunoglobulin proteins; they may also purified by the removal of immunoglobulin that does not bind the antigen of interest (e.g., at least a portion of Factor VIII). The removal of non-immunoglobulin proteins and/or the removal of immunoglobulins that do not bind the antigen of interest (e.g., at least a portion of Factor VIII) results in an increase in the percent of desired antigen-reactive immunoglobulins in the sample. In another example, recombinant polypeptides of Factor VIII are expressed in bacterial host cells and the polypeptides are purified by the removal of host cell proteins; the percent of recombinant polypeptides is thereby increased in the sample.

As used herein, the term "chimeric protein" refers to two or more coding sequences obtained from different genes, that have been cloned together and that, after translation, act as a single polypeptide sequence. Chimeric proteins are also referred to as "hybrid proteins." As used herein, the term "chimeric protein" refers to coding sequences that are obtained from different species of organisms, as well as coding sequences that are obtained from the same species of organisms.

A "composition comprising a given polynucleotide sequence" as used herein refers broadly to any composition containing the given polynucleotide sequence. The composition may comprise an aqueous solution.

As used herein, the term "at risk" is used in references to individuals who are at risk for experiencing hemorrhagic episodes. In particularly preferred embodiments, the individuals are hemophiliacs with mild, moderate, or severe hemophilia.

As used herein, the term "subject" refers to any animal (i.e., vertebrates and invertebrates), while the term "vertebrate subject" refers to any member of the subphylum Chordata. It is intended that the term encompass any member of this subphylum, including, but not limited to humans and other primates, rodents (e.g., mice, rats, and guinea pigs), lagamorphs (e.g., rabbits), bovines (e.g, cattle), ovines (e.g., sheep), caprines (e.g., goats), porcines (e.g., swine), equines (e.g., horses), canines (e.g., dogs), felines (e.g., cats), domestic fowl (e.g., chickens, turkeys, ducks, geese, other gallinaceous birds, etc.), as well as feral or wild animals, including, but not limited to, such animals as ungulates (e.g., deer), bear, fish, lagamorphs, rodents, birds, etc. It is not intended that the term be limited to a particular age or sex. Thus, adult and newborn subjects, as well as fetuses, whether male or female, are encompassed by the term.

As defined herein, a "therapeutically effective amount" or "therapeutic effective dose" is an amount or dose of AAV vector or virions capable of producing sufficient amounts of Factor VIII to decrease the time it takes for a subject's blood to clot. Generally, severe hemophiliacs having less than 1% of normal levels of FVIII have a whole blood clotting time of greater than 60 minutes as compared to approximately 10 minutes for non-hemophiliacs.

DETAILED DESCRIPTION OF THE INVENTION

The present invention relates to AAV vectors suitable for hemophilia A gene therapy. More particularly, these AAV vectors are suitable for delivering nucleic acids encoding Factor VIII into a recipient host suspected of suffering from a blood clotting disorder. Using the nucleic acid as a template, the host produces Factor VIII, such that the subject's blood is able to clot. The present invention also provides pharmaceutical compositions comprising such AAV vectors, as well as methods for making and using the constructs.

I. AAV Vectors

Adeno-associated virus (AAV) is a non-pathogenic, replication-defective, helper-dependent parvovirus (or "dependovirus" or "adeno-satellite virus"). There are at least six recognized serotypes, designated as AAV-1, AAV-2, AAV-3, AAV-4, AAV-5, AAV-X7, etc. Culture and serologic evidence indicates that human infection occurs with AAV-2 and AAV-3. Although 85% of the human population is seropositive for AAV-2, the virus has never been associated with disease in humans. Recombinant AAV (rAAV) virions are of interest as vectors for gene therapy because of their broad host range, excellent safety profile, and duration of transgene expression in infected hosts. One remarkable feature of recombinant AAV (rAAV) virions is the prolonged expression achieved after in vivo administration.

AAV vectors of the present invention may be constructed using known techniques to provide, as operatively linked components in the direction of transcription, (a) control sequences including a transcriptional initiation and termination regions, and (b) a nucleotide sequence encoding at least a portion of Factor VIII. The control sequences are selected to be functional in a targeted recipient cell. The resulting construct which contains the operatively linked components is bounded (5' and 3') with functional AAV ITR sequences.

The nucleotide sequences of AAV ITR regions are known (See e.g., Kotin, Hum. Gene Ther., 5:793–801 [1994]; Berns, "Parvoviridae and Their Replication" in Fields and Knipe (eds), *Fundamental Virology,* 2nd Edition, for the AAV-2 sequence). AAV ITRs used in the vectors of the invention need not have a wild-type nucleotide sequence, and may be altered (e.g., by the insertion, deletion or substitution of nucleotides). Additionally, AAV ITRs may be derived from any of several AAV serotypes, including without limitation, AAV-1, AAV-2, AAV-3, AAV-4, AAV-5, AAVX7, etc. Furthermore, 5' and 3' ITRs which flank a selected nucleotide sequence in an AAV vector need not necessarily be identical or derived from the same AAV serotype or isolate, so long as they function as intended.

A. Control Sequences

In some embodiments of the present invention, heterologous control sequences are employed with the vectors. Useful heterologous control sequences generally include those derived from sequences encoding mammalian or viral genes. Examples include, but are not limited to, the SV40 early promoter, mouse mammary tumor virus LTR promoter, adenovirus major late promoter (Ad MLP), a herpes simplex virus (HSV) promoter, a cytomegalovirus (CMV) promoter such as the CMV immediate early promoter region (CMVIE), a rous sarcoma virus (RSV) promoter, synthetic promoters, hybrid promoters, and the like. In addition, sequences derived from nonviral genes, such as the murine metallothionein gene, also find use herein. Such promoter sequences are commercially available (e.g., from Stratagene).

It is contemplated that in some embodiments, tissue-specific expression may be desirable (e.g., expression of biologically active Factor VIII by hepatocytes). It is not intended that the present invention be limited to expression of biologically active Factor VIII by any particular cells or cell types. However, as hepatocytes (i.e., liver cells) are the cells that normally synthesized Factor VIII (See, Kaufman, Ann. Rev. Med., 43:325 [1992]), it is contemplated that in some particularly preferred embodiments, the compositions of the present invention be administered to the liver.

In preferred embodiments, expression is achieved by coupling the coding sequence for Factor VIII with heterologous control sequences derived from genes that are specifically transcribed by a selected tissue type. A number of tissue-specific promoters have been described above which enable directed expression in selected tissue types. However, control sequences used in the present AAV vectors can also comprise control sequences normally associated with the selected nucleic acid sequences.

B. Construction of AAV Factor VIII Vectors

AAV vectors that contain a control sequence and a nucleotide sequence of interest (i.e., at least a portion of the sequence encoding Factor VIII), bounded by AAV ITRs (i.e., AAV vectors), can be constructed by directly inserting selected sequences into an AAV genome with the major AAV open reading frames ("ORFs") excised. Other portions of the AAV genome can also be deleted, so long as a sufficient portion of the ITRs remain to allow for replication and packaging functions. These constructs can be designed using techniques well known in the art (See e.g., U.S. Pat. Nos. 5,173,414 and 5,139,941, all of which are herein incorporated by reference); International Publication Nos. WO 92/01070 and WO 93/03769; Lebkowski et al., Mol. Cell. Biol., 8:3988–3996 [1988]; Vincent et al., Vaccines 90 [Cold Spring Harbor Laboratory Press, 1990]; Carter, Curr. Opin. Biotechnol., 3:533–539 [1992]; Muzyczka, Curr. Top. Microbiol. Immunol., 158:97–129 [1992]; Kotin, Hum. Gene Ther., 5:793–801 [1994]; Shelling and Smith, Gene Ther., 1:165–169 [1994]; and Zhou et al., J. Exp. Med., 179:1867–1875 [1994]).

Alternatively, AAV ITRs can be excised from the viral genome or from an AAV vector containing the same and fused 5' and 3' of a selected nucleic acid construct that is present in another vector using standard ligation techniques, such as those described in Sambrook et al., supra. For example, ligations can be accomplished in 20 mM Tris-Cl pH 7.5, 10 mM MgCl$_2$, 10 mM DTT, 33 μg/ml BSA, 10 mM-50 mM NaCl, and either 40 μM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 30–100 μg/ml total DNA concentrations (5–100 nM total end concentration). AAV vectors which contain ITRs have been described in (e.g., U.S. Pat. No. 5,139,941, herein incorporated by reference). In particular, several AAV vectors are described therein which are available from the American Type Culture Collection ("ATCC") under Accession Numbers 53222, 53223, 53224, 53225 and 53226.

Additionally, chimeric genes can be produced synthetically to include AAV ITR sequences arranged 5' and 3' of a selected nucleic acid sequence. The complete chimeric sequence is assembled from overlapping oligonucleotides prepared by standard methods (See e.g., Edge, Nature 292:756 [1981]; Nambair et al., Science 223:1299 [1984]; and Jay et al., J. Biol. Chem., 259:6311 [1984]).

Moreover, it is not intended that the present invention be limited to any specific Factor VIII sequence. Many natural and recombinant forms of Factor VIII have been isolated and assayed both in vitro and in vivo, using a variety of different regulatory elements and control sequences. Therefore, any known, or later discovered, DNA sequence coding for biologically active Factor VIII can be expressed, alone or in combination with at least one additional vector, using the AAV vectors and methods taught in the present invention. Examples of naturally occurring and recombinant forms of Factor VIII can be found in the patent and scientific literature including, U.S. Pat. No. 5,563,045, U.S. Pat. No. 5,451,521, U.S. Pat. No. 5,422,260, U.S. Pat. No. 5,004,803, U.S. Pat. No. 4,757,006, U.S. Pat. No. 5,661,008, U.S. Pat. No. 5,789,203, U.S. Pat. No. 5,681,746, U.S. Pat. No. 5,595,886, U.S. Pat. No. 5,045,455, U.S. Pat. No. 5,668,108, U.S. Pat. No. 5,633,150, U.S. Pat. No. 5,693,499, U.S. Pat. No. 5,587,310, U.S. Pat. No. 5,171,844, U.S. Pat. No. 5,149,637, U.S. Pat. No. 5,112,950, U.S. Pat. No. 4,886,876, WO 94/11503, WO 87/07144, WO 92/16557, WO 91/09122, WO 97/03195, WO 96/21035, WO 91/07490, EP 0 672 138, EP 0 270 618, EP 0 182 448, EP 0 162 067, EP 0 786 474, EP 0 533 862, EP 0 506 757, EP 0 874 057, EP 0 795 021, EP 0 670 332, EP 0 500 734, EP 0 232 112, EP 0 160 457, Sanberg et al., XXth Int. Congress of the World Fed. Of Hemophilia (1992), and Lind et al., Eur. J. Biochem., 232:19 (1995).

Nucleic acid sequences coding for the above-described Factor VIII can be obtained using recombinant methods, such as by screening cDNA and genomic libraries from cells expressing Factor VIII or by deriving the sequence from a vector known to include the same. Furthermore, the desired sequence can be isolated directly from cells and tissues containing the same, using standard techniques, such as phenol extraction and PCR of cDNA or genomic DNA (See e.g., Sambrook et al., supra, for a description of techniques used to obtain and isolate DNA). Nucleotide sequences encoding an antigen of interest (i.e., Factor VIII sequence) can also be produced synthetically, rather than cloned. The complete sequence can be assembled from overlapping oligonucleotides prepared by standard methods and assembled into a complete coding sequence (See e.g., Edge, Nature 292:756 [1981]; Nambair et al., Science 223:1299 [1984]; and Jay et al., J. Biol. Chem., 259:6311 [1984]).

Although it is not intended that the present invention be limited to any particular methods for assessing the production of biologically active Factor VIII, such methods as immunoassays (e.g., ELISA) and biological activity assays are contemplated (e.g., coagulation activity assays).

Furthermore, while in particularly preferred embodiments, human Factor VIII is encompassed by the present invention, it is not intended that the present invention be limited to human Factor VIII. Indeed, it is intended that the present invention encompass Factor VIII from animals other than humans, including but not limited to companion animals (e.g., canines, felines, and equines), livestock (e.g., bovines, caprines, and ovines), laboratory animals (e.g., rodents such as murines, as well as lagamorphs), and "exotic" animals (e.g., marine mammals, large cats, etc.).

II. Virion Production

Producing AAV Factor VIII vectors and rAAV Factor VIII virions of the present invention generally involve the steps of: (1) introducing an AAV vector containing the Factor VIII gene into a host cell; (2) introducing an AAV helper construct into the host cell, where the helper construct includes AAV coding regions capable of being expressed in the host cell to complement AAV helper functions missing from the AAV vector; (3) introducing one or more helper viruses and/or accessory function vectors into the host cell, wherein the helper virus and/or accessory function vectors provide accessory functions capable of supporting efficient recombinant AAV ("rAAV") virion production in the host cell; and (4) culturing the host cell to produce rAAV virions.

The above-described vectors and constructs can be introduced into a cell using standard methodology known to those of skill in the art (e.g., transfection). A number of transfection techniques are generally known in the art (See e.g., Graham el al., Virol., 52:456 [1973], Sambrook et al. supra, Davis et al., supra, and Chu et al., Gene 13:197 [1981]). Particularly suitable transfection methods include calcium phosphate co-precipitation (Graham et al., Virol., 52:456–467 [1973]), direct micro-injection into cultured cells (Capecchi, Cell 22:479–488 [1980]), electroporation (Shigekawa et al., BioTechn., 6:742–751 [1988]), liposome-mediated gene transfer (Mannino et al., BioTechn., 6:682–690 [1988]), lipid-mediated transduction (Felgner et al., Proc. Natl. Acad. Sci. U.S.A. 84:7413–7417 [1987]), and nucleic acid delivery using high-velocity microprojectiles (Klein et al., Nature 327:70–73 [1987]).

For the purposes of the invention, suitable host cells for producing rAAV virions include microorganisms, yeast cells, insect cells, and mammalian cells, that can be, or have been, used as recipients of a heterologous DNA molecule. The term includes the progeny of the original cell which has been transfected. Thus, as indicated above, a "host cell" as used herein generally refers to a cell which has been transfected with an exogenous DNA sequence. Cells from the stable human cell line, 293 (ATCC Accession No. CRL1573) are preferred in the practice of the present invention. Particularly, the human cell line 293 is a human embryonic kidney cell line that has been transformed with adenovirus type-5 DNA fragments (Graham et al., J. Gen. Virol., 36:59 [1977]), and expresses the adenoviral E1a and E1b genes (Aiello et al., Virol., 94:460 [1979]). The 293 cell line is readily transfected, and provides a particularly convenient platform in which to produce rAAV virions.

Host cells containing the above-described AAV vectors must be rendered capable of providing AAV helper functions in order to replicate and encapsidate the nucleotide sequences flanked by the AAV ITRs to produce rAAV virions. AAV helper functions are generally AAV-derived coding sequences which can be expressed to provide AAV gene products that, in turn, function in trans for productive AAV replication. AAV helper functions are used herein to complement necessary AAV functions that are missing from the AAV vectors. Thus, AAV helper functions include one, or both of the major AAV ORFs, namely the rep and cap coding regions, or functional homologues thereof.

AAV helper functions are introduced into the host cell by transfecting the host cell with an AAV helper construct either prior to, or concurrently with, the transfection of the AAV vector. AAV helper constructs are thus used to provide at least transient expression of AAV rep and/or cap genes to complement missing AAV functions that are necessary for productive AAV infection. AAV helper constructs lack AAV ITRs and can neither replicate nor package themselves.

In preferred embodiments, these constructs are in the form of a vector, including, but not limited to, plasmids, phages, transposons, cosmids, viruses, or virions. A number of AAV helper constructs have been described, such as the commonly used plasmids pAAV/Ad and pIM29+45 which encode both Rep and Cap expression products (See e.g., Samulski et al., J. Virol,. 63:3822–3828 [1989]; and McCarty et al., J. Virol., 65:2936–2945 [1991]). A number of other vectors have been described which encode Rep and/or Cap expression products (See e.g., U.S. Pat. No. 5,139,941, herein incorporated by reference).

Both AAV vectors and AAV helper constructs can be constructed to contain one or more optional selectable markers. Suitable markers include genes which confer antibiotic resistance or sensitivity to, impart color to, or change the antigenic characteristics of those cells which have been transfected with a nucleic acid construct containing the selectable marker when the cells are grown in an appropriate selective medium. Several selectable marker genes that are useful in the practice of the invention include the gene encoding aminoglycoside phosphotranferase (APH) that allows selection in mammalian cells by conferring resistance to G418 (Sigma). Other suitable markers are known to those of skill in the art.

The host cell (or packaging cell) must also be rendered capable of providing non-AAV derived functions, or "accessory functions," in order to produce rAAV virions. Accessory functions are non-AAV derived viral and/or cellular functions upon which AAV is dependent for its replication. Thus, accessory functions include at least those non-AAV proteins and RNAs that are required in AAV replication, including those involved in activation of AAV gene transcription, stage specific AAV mRNA splicing, AAV DNA replication, synthesis of rep and cap expression products and AAV capsid assembly. Viral-based accessory functions can be derived from any of the known helper viruses.

Particularly, accessory functions can be introduced into and then expressed in host cells using methods known to those of skill in the art. Commonly, accessory functions are provided by infection of the host cells with an unrelated helper virus. A number of suitable helper viruses are known, including adenoviruses; herpesviruses such as herpes simplex virus types 1 and 2; and vaccinia viruses. Nonviral accessory functions will also find use herein, such as those provided by cell synchronization using any of various known agents (See e.g., Buller et al., J. Virol., 40:241–247 [1981]; McPherson et al., Virol., 147:217–222 [1985]; and Schlehofer et al., Virol., 152:110–117 [1986]).

Alternatively, accessory functions can be provided using an accessory function vector. Accessory function vectors include nucleotide sequences that provide one or more accessory functions. An accessory function vector is capable of being introduced into a suitable host cell in order to support efficient AAV virion production in the host cell. Accessory function vectors can be in the form of a plasmid, phage, virus, transposon or cosmid. Accessory vectors can also be in the form of one or more linearized DNA or RNA fragments which, when associated with the appropriate control sequences and enzymes, can be transcribed or expressed in a host cell to provide accessory functions.

Nucleic acid sequences providing the accessory functions can be obtained from natural sources, such as from the genome of adenovirus, or constructed using recombinant or synthetic methods known in the art. In this regard, adenovirus-derived accessory functions have been widely studied, and a number of adenovirus genes involved in accessory functions have been identified and partially characterized (See e.g., Carter, "Adeno-Associated Virus Helper Functions," in *CRC Handbook of Parvoviruses*, Vol. I (P. Tijssen, ed.) [1990], and Muzyczka, Curr. Top. Microbiol. Immun., 158:97–129 [1992]). Specifically, early adenoviral gene regions E1a, E2a, E4, VAI RNA and, possibly, E1b are thought to participate in the accessory process (Janik et al., Proc. Natl. Acad. Sci. U.S.A. 78:1925–1929 [1981]). Herpesvirus-derived accessory functions have been described (See e.g., Young et al., Prog. Med. Virol., 25:113 [1979]). Vaccinia virus-derived accessory functions have also been described (See e.g., Carter, supra., and Schlehofer et al., Virol., 152:110–117 [1986]).

As a consequence of the infection of the host cell with a helper virus, or transfection of the host cell with an accessory function vector, accessory functions are expressed which transactivate the AAV helper construct to produce AAV Rep and/or Cap proteins. The Rep expression products direct excision of the recombinant DNA (including the DNA of interest encoding at least a portion of Factor VIII) from the AAV vector. The Rep proteins also serve to duplicate the AAV genome. The expressed Cap proteins assemble into capsids, and the recombinant AAV genome is packaged into the capsids. Thus, productive AAV replication ensues, and the DNA is packaged into rAAV virions.

Following recombinant AAV replication, rAAV virions can be purified from the host cell using a variety of conventional purification methods, such as CsCl gradients. Further, if helper virus infection is employed to express the accessory functions, residual helper virus can be inactivated, using known methods. For example, adenovirus can be inactivated by heating to temperatures of approximately 60° C. for approximately 20 minutes or more, as appropriate. This treatment selectively inactivates the helper adenovirus which is heat labile, while preserving the rAAV which is heat stable.

III. Pharmaceutical Compositions

The resulting rAAV virions are then ready for use in pharmaceutical compositions which can be delivered to a subject, so as to allow production of biologically active Factor VIII. Pharmaceutical compositions comprise sufficient genetic material that allows the recipient to produce a therapeutically effective amount of Factor VIII so as to reduce, stop and/or prevent hemorrhage. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, clotting factors or factor precursors, drugs or hormones. In preferred embodiments, the pharmaceutical compositions also contain a pharmaceutically acceptable excipient. Such excipients include any pharmaceutical agent that does not itself induce an immune response harmful to the individual receiving the composition, and which may be administered without undue toxicity. Pharmaceutically acceptable excipients include, but are not limited to, liquids such as water, saline, glycerol, sugars and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in *Remington's Pharmaceutical Sciences* (Mack Pub. Co., 18th Edition, Easton, Pa. [1990]).

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art (e.g., by means of conventional mixing, dissolving, granulating, dragee-making, levigating, emulsifying, encapsulating, entrapping, or lyophilizing processes).

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding, free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment. For administration of Factor VIII-containing vectors, such labeling would include amount, frequency, and method of administration.

Pharmaceutical compositions suitable for use in the invention include compositions wherein the active ingredients are contained in an effective amount to achieve the intended purpose. Determining a therapeutic effective dose is well within the capability of those skilled in the art using the techniques taught in the present invention, such as ELISA and ChromZ FVIII coagulation activity assay, and other techniques known in the art. Therapeutic doses will depend on, among other factors, the age and general condition of the subject, the severity of hemophilia, and the strength of the control sequences. Thus, a therapeutically effective amount in humans will fall in a relatively broad range that can be determined through clinical trials.

It is intended that the dosage treatment and regimen used with the present invention will vary, depending upon the subject and the preparation to be used. Thus, the dosage treatment may be a single dose schedule or a multiple dose schedule. Moreover, the subject may be administered as many doses as appropriate to achieve or maintain the desired blood clotting time.

Direct delivery of the pharmaceutical compositions in vivo will generally be accomplished via injection using a conventional syringe, although other delivery methods such as convention-enhanced delivery are envisioned (See e.g., U.S. Pat. No. 5,720,720, incorporated herein by reference). In this regard, the compositions can be delivered subcutaneously, epidermally, intradermally, intrathecally, intraorbitally, intramucosally (e.g., nasally, rectally and vaginally), intraperitoneally, intravenously, intraarterially, orally, or intramuscularly. Other modes of administration include oral and pulmonary administration, suppositories, and transdermal applications. In particularly preferred embodiments, the compositions are administered intravenously in the portal vasculature or hepatic artery One skilled in the art will recognize that the methods and compositions described above are also applicable to a range of other treatment regimens known in the art. For example, the methods and compositions of the present invention are compatible with ex vivo therapy (e.g., where cells are removed from the body, incubated with the AAV vector and the treated cells are returned to the body).

IV. Administration

AAV vector can be administered to any tissue suitable for the expression of factor VIII. In a preferred embodiments, the AAV vectors of the present invention are successfully administered via the portal vasculature or hepatic artery where it is thought, without being bound by theory, that the vector transduces hepatocytes. Current approaches to targeting genes to the liver have focused upon ex vivo gene therapy. Ex vivo liver-directed gene therapy involves the surgical removal of liver cells, transduction of the liver cells in vitro (e.g., infection of the explanted cells with recombinant retroviral vectors) followed by injection of the genetically modified liver cells into the liver or spleen of the patient. A serious drawback for ex vivo gene therapy of the liver is the fact that hepatocytes cannot be maintained and expanded in culture. Therefore, the success of ex vivo liver-directed gene therapy depends upon the ability to efficiently and stably engraft the genetically modified (i.e., transduced) hepatocytes and their progeny. It has been reported that even under optimal conditions, autologous modified liver cells injected into the liver or spleen which engraft represent only a small percentage (less than 10%) of the total number of cells in the liver. Ectopic engraftment of transduced primary hepatocytes into the peritoneal cavity has been tried, in order to address the problem of engraftment in the liver.

Given the problems associated with ex vivo liver-directed gene therapy, in vivo approaches have been investigated for the transfer of genes into hepatocytes, including the use of recombinant retroviruses, recombinant adenoviruses, liposomes and molecular conjugates. While these in vivo approaches do not suffer from the drawbacks associated with ex vivo liver-directed gene therapy, they do not provide a means to specifically target hepatocytes. In addition, several of these approaches require performance of a partial hepatectomy, in order to achieve prolonged expression of the transferred genes in vivo. Adenovirus and molecular conjugate based delivery methods also result in liver toxicity and inflammation which is an undesirable feature of Factor VIII gene therapy. The present invention provides compositions and methods for the long-term expression of biologically active Factor VIII. It is contemplated that the present invention will bypass the need for partial hepatectomy, while allowing expression of Factor VIII in concentrations that are therapeutic in vivo. The present invention further provides gene therapy compositions and methods that target hepatocytes for the production of Factor VIII by treated individuals.

Other tissues, however, may be suitable for the expression of Factor VIII even if they are not the tissue that normally synthesizes the protein. Muscle cells, for example, have been shown to express biologically active blood clotting Factor IX even though it is normally synthesized in the liver.

Finally, the AAV vectors may contain any nucleic acid sequences coding for biologically active Factor VIII. Additionally, the AAV vectors may contain a nucleic acid coding for fragments of Factor VIII which is itself not biologically active, yet when administered into the subject improves or restores the blood clotting time. For example, as discussed above, the Factor VIII protein comprises two polypeptide chains: a heavy chain and a light chain separated by a B-domain which is cleaved during processing. As demonstrated by the present invention, co-transducing recipient cells with the Factor VIII heavy and light chains leads to the expression of biologically active Factor VIII. Because, however, most hemophiliacs contain a mutation or deletion in only one of the chains (e.g., heavy or light chain), it may be possible to administer only the chain defective in the patient and allow the patient to supply the other chain. In this case, the AAV vector would fall within the scope of the invention even though the single chain (i.e., heavy or light) would not be biologically active until it was administered into a subject which can supply the second chain, thus forming biologically active Factor VIII.

V. Factor VIII Aassays

As described in the Experimental section below, there are many ways to assay Factor VIII expression and activity. Although the present invention is not limited to immunoassay methods, the present invention also provides methods for detecting Factor VIII expression comprising the steps of: a) providing a sample suspected of containing Factor VIII, and a control containing a known amount of known Factor VIII; and b) comparing the test sample with the known control, to determine the relative concentration of Factor VIII in the sample. Thus, the methods are capable of identifying samples (e.g., patient samples) with sufficient or insufficient quantities of Factor VIII. In addition, the methods may be conducted using any suitable means to determine the relative concentration of Factor VIII in the test and control samples, including but not limited to means selected from the group consisting of Western blot analysis, Northern blot analysis, Southern blot analysis, denaturing polyacrylamide gel electrophoresis (e.g., SDS-PAGE), reverse transcriptase-coupled polymerase chain reaction (RT-PCR), enzyme-linked immunosorbent assay (ELISA), radioimmunoassay (RIA), and fluorescent immunoassay (IFA). Thus, the methods may be conducted to determine the presence of normal Factor VIII sequences in the genome of the animal source of the test sample, or the expression of Factor VIII (mRNA or protein), as well as detect the presence of abnormal or mutated Factor VIII gene sequences in the test samples.

In one preferred embodiment, the presence of Factor VIII is detected by immunochemical analysis. For example, the immunochemical analysis can comprise detecting binding of an antibody specific for an epitope of Factor VIII. In one another preferred embodiment of the method, the antibody comprises polyclonal antibodies, while in another preferred embodiment, the antibody comprises monoclonal antibodies.

It is further contemplated that antibodies directed against at least a portion of Factor VIII will be used in methods known in the art relating to the localization and structure of Factor VIII (e.g., for Western blotting), measuring levels thereof in appropriate biological samples, etc. The antibodies can be used to detect Factor VIII in a biological sample from an individual (e.g., an individual treated using the methods and/or compositions of the present invention). The biological sample can be a biological fluid, including, but not limited to, blood, serum, plasma, interstitial fluid, urine, cerebrospinal fluid, synovial fluid, and the like. In particular, the antigen can be detected from cellular sources, including, but not limited to, hepatocytes. For example, cells can be obtained from an individual and lysed (e.g., by freeze-thaw cycling, or treatment with a mild cytolytic detergent including, but not limited to, TRITON X-100, digitonin, NONIDET P (NP)-40, saponin, and the like, or combinations thereof, See, e.g., International Patent Publication WO 92/08981).

The biological samples can then be tested directly for the presence of the Factor VIII using an appropriate strategy (e.g., ELISA or RIA) and format (e.g., microwells, dipstick [e.g., as described in International Patent Publication WO 93/03367], etc.). Alternatively, proteins in the sample can be size separated (e.g., by polyacrylamide gel electrophoresis (PAGE), with or without sodium dodecyl sulfate (SDS), and the presence of Factor VIII detected by immunoblotting [e.g., Western blotting]). Immunoblotting techniques are generally more effective with antibodies generated against a peptide corresponding to an epitope of a protein, and hence, are particularly suited to the present invention. In another preferred embodiment, the level of Factor VIII is assayed using the whole-blood clotting time and activated parial thromboplastin time (aPTT) of the subject's blood using techniques well known in the art (Herzog et al., Nature Medicine 5:56 [1999]).

The foregoing explanations of particular assay systems are presented herein for purposes of illustration only, in fulfillment of the duty to present an enabling disclosure of the invention. It is to be understood that the present invention contemplates a variety of immunochemical assay protocols within its spirit and scope. Indeed, other methods such as biological assays to determine the presence and activity of Factor VIII are also encompassed by the present invention.

Thus, in addition to the immunoassay systems described above, other assay systems, such as those designed to measure and/or detect Fraction VIII and/or clotting ability of a subject's blood are also encompassed by the present invention (e.g., the ChromZ FVIII coagulation activity [FVIII-c] assay [Helena Labs]).

Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

In the experimental disclosure which follows, the following abbreviations apply: N (Normal); M (Molar); mM (millimolar); μM (micromolar); g (grams); mg (milligrams); μg (micrograms); ng (nanograms); l or L (liters); ml (milliliters); μl (microliters); cm (centimeters); mm (millimeters); μm (micrometers); nm (nanometers); mU (milliunits); $^{51}$Cr (Chromium 51); μCi (microcurie); EC (degrees Centigrade); hFVIII (human factor VIII); FVIII (factor VIII); pH (hydrogen ion concentration); JRH grade; NaCl (sodium chloride); HCl (hydrochloric acid); OD (optical density); bp (base pair(s)); ATP (adenosine 5'-triphosphate); PCR (polymerase chain reaction); DNA (deoxyribonucleic acid); cDNA (complementary DNA); AAV (adeno-associated virus); rAAV (recombinant adeno-associated virus); ITR (inverted terminal repeat); FCS or FBS (fetal calf serum; fetal bovine serum); CFA (complete Freund's adjuvant); BSA (bovine serum albumin); ATCC (American Type Culture Collection, Rockville, Md.); Sigma (Sigma Aldrich, St. Louis, Mo.); Biodesign International (Biodesign International, Kennebunk, Mich.); Baxter Hyland (Baxter Healthcare Corp., Biotech Group—Hyland Division, Hayward, Calif.); Helena Labs (Helena Laboratories, Beaumont, Tex.); American Diagnostica (American Diagnostica, Greenwich, Conn.); Accurate Chemical (Accurate Chemical and Scientific Corp., Westbury, N.Y.); Molecular Probes (Molecular Probes, Eugene, Oreg.); Vysis (Vysis, Downer Grove, Ill.); Tel-Test (Tel-Test, Inc., Friendswood, Tex.); Molecular Dynamics Molecular Dynamics, Sunnyvale, Calif.); NUNC (Naperville, Ill.); and Stratagene (Stratagene Cloning Systems, La Jolla, Calif.); Affinity Biologicals (Affinity Biologicals, Inc., Hamilton, Ontario); and Biodesign (Biodesign International, Keinmebunkport, Me.).

EXAMPLE 1

Dual Vector Plasmid Construction

The heavy and light chains of human Factor VIII (hFVIII) were assembled according to those reported by Yonemura et al (Yonemura et al., Prot. Engineer., 6:669–674 [1993]) and cloned as expression cassettes into AAV vectors. Both vectors contain the promoter and the first non-coding intron (from −573 to +985) from the human elongation factor 1α (EF1α) gene (Uetsuki et al, J. Biol. Chem., 264:5791–5798 [1989]; and Kim et al., Gene 9:217–223 [1990]). Each vector also contains the first 57 base pairs of the FVIII heavy chain encoding the 19 amino acid signal sequence. The heavy chain construct encodes the A1 and A2 domains and 5 amino acids from the N terminus of the B domain. The light chain vector encodes 85 amino acids of the carboxy terminal B domain, in addition to the A3, C1, and C2 domains. Both vectors utilize the human growth hormone (hGfl) polyadenylation signal. The expression cassettes were inserted between AAV ITRs. The initial cloning step involved deleting 854 bp of EF1α sequences between the SpeI and XcmI sites of pVm4.1e-hFIX (Nakai et al., Blood 91:1–9 [1998]), and religating to create pVm4.1eδD-hFIX.

This construct was then digested with EcoRI, which released the hFIX cDNA, and was ligated to an oligonucleotide containing MfeI ends (EcoRI-compatible) and an internal ClaI restriction site, creating pVm4.1eδD-linker. The heavy and light chain fragments, including the hGH polyadenylation sequences were isolated from pVm4.1cFVIII-HC and pVm4.1cFVIII-LC, respectively as ClaI-BstEII fragments. These fragments were cloned between the corresponding sites in the pVm4.1eδD-linker, creating plasmids pVm4.1eδD-FVIII-HC (also, rAAV-hFVIII-HC) and pVm4.1eδD-FVIII-LC (also, rAAV-hFVIII-LC).

Figure 7:
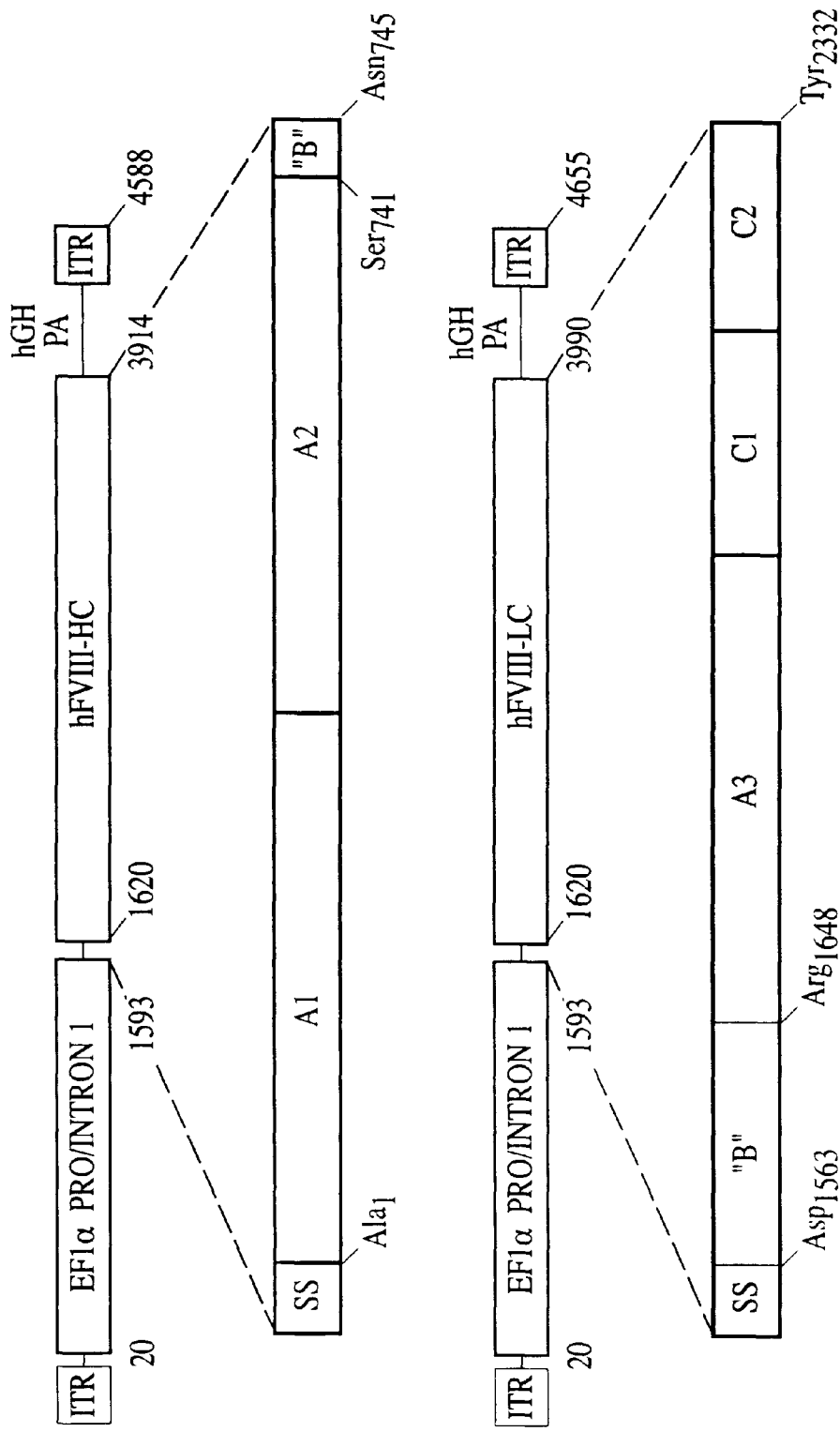
FIG. 7 provides a map of rAAV-hFVIII-HC and rAAV-hFVIII-LC vectors.

FIG. 7 provides a map of the constructs. In this figure, the upper line in each panel represents the gene structure of the vectors, and the lower line represents the structure of the hFVIII protein domains enconded by the vectors (ITR, AAV inverted terminal repeat; EF1α Pro/Intron 1, human polypeptide elongation factor 1 α gene promoter and first intron; hFVIII-HC human FVIII cDNA; hFVIII-LC, human FVIII cDNA; hGH PA, human growth hormone polyadenylation signal; SS, human FVIII signal sequence; A1, A2, "B", A3, C1, C2, complete and incomplete (') protein domains of the hFVIII protein).

EXAMPLE 2

Single Vector Plasmid Construction

The plasmid pAAV-F8-1 construct containing both the light and heavy chains of factor VIII was constructed as follows. A PCR fragment, Z8, containing cloning sites, 5'-splicing donor site of a synthetic intron based on EF1α and immunoglobulin G (IgG) intron sequences, Kozak sequence and the first 16 nucleotides of the human blood coagulation factor VIII (FVIII) coding sequence was generated using oligonucleotides Z8S and Z8A. The sequences of the nucleic acids is shown below:
Oligonucleotide Z8S:
  5' cccaagcttgcggccgcccgggtgccgc-ccctaggcaggtaagtgccgtgtgtggttcc 3' (SEQ ID NO:1)
Oligonucleotide Z8A:
  5' ccgctcgagcagagctctatttgcatg-gtggaatcgatgccgcgggaaccacacacggc 3' (SEQ ID NO:2)
PCR fragment Z8:
  5' cccaagcttgcggccgcccgggtgccgc-ccctaggcaggtaagtgccgtgtgtggt-tcccgcggcatcgattccaccatgcaaatagagctctgctcgagcgg 3' (SEQ ID NO:3)

Nucleic acid Z8 was inserted into pZERO-2 (Invitrogen) between HindIII and XhoI sites to create pZ8. A PCR fragment, INT3, containing the branching point, the polypyrimidine tract, and the 3' splicing acceptor site of the synthetic intron was generated using oligonucleotides INT3S and INT3A whose sequence is shown below.
Oligonucleotide INT3S:
  5' ttcccgcgggcctggcctctttacgggt-tatggcccttgcgtgccttgaattactga 3' (SEQ ID NO:4)
Oligonucleotide INT3A:
  5' gaatcgatacctgtggagaaaaa-gaaaagtggatgtcagtgtcagtaattcaaggc 3' (SEQ ID NO:5)
PCR Fragment INT3:
  5' ttcccgcgggcctggcctctttacgggt-tatggcccttgcgtgccttgaattact-gacactgacatccactttttctttttctccacaggtatcgattc 3' (SEQ ID NO:6)

INT3 was inserted between the SacII and ClaI sites of pZ8 to create pZ8.I. Therefore, Z8.I contains the entire synthetic intron between AvrII and ClaI sites. A hFVIII cDNA fragment having SacI and XhoI restriction sites was inserted between the SacI and XhoI sites of pZ8.I to create pZ8.I.dB. Therefore, pZ8.I.dB contains a synthetic intron and the entire coding sequence of hFVIII.

A PCR fragment, EG3, containing three HNF-3 binding sites and −54 to +8 of mouse albumin gene was generated using oligonucleotides EG3S and EG3A with modifications to eliminate linker sequences. The sequences of EG3S and EG3A are as follows:
Oligonucleotide EG3S:
  5' aggaatgtttgttcttaaataccatc-caggcaatgtttgttcttaattaccatc-cagggaatetttcttcttaaataccatctacagttattggttaaa 3' (SEQ ID NO:7)
Oligonucleotide EG3A:
  5' ggaaaggtgatctgtgtgcagaaa-gactcgctctaatatacttctttaaccaataactg 3' (SEQ ID NO:8)
PCR Fragment EG3:
  5' agggaatgtttgttcttaaataccatc-cagggaatgtttgttcttaaataccatc-cagggaatgtttttcttaaataccatc-tacagttattggttaaagaagtatattagagcgagtcttctgcacacagatcaccttttcc 3' (SEQ ID NO:9)

EG3 was then phosphorylated using T4 polynucleotide kinase and inserted into the SmaI site of pZ8.I.dB to create pZ8.I.dB.egg. A DNA fragment, SPA, containing an efficient synthetic polyA signal based on rabbit β-globin sequences (Levitt et al., Genes and Develop., 3:1019 [1989]) was generated by hybridizing two oligonucleotides SPA.S and SPA.A.
Oligonucleotide SPA.S:
  5' tcgagaataaaagatcagagctcta-gagatctgtgtgttggttttttgtgtgcggccgc 3' (SEQ ID NO:10)
Oligonucleotide SPA.A:
  5' tcgagcggccgcacacaaaaaaccaaca-cacagatctctagagctctgatctttattc 3' (SEQ ID NO:11)
PCR Fragment SPA:
  5' tcgagaataaaagatcagagctcta-gagatctgtgtgttggttttttgtgtgcggccgctcga 3' (SEQ ID NO:12)

SPA was inserted into the XhoI site of pZero-2 to create pZero-2.SPA. SPA was excised from a pZero-2.SPA clone and inserted into the XhoI site of pZ8.I.dB.egg to create pZ8.I.dB.egg.A. pAAV-CMV-FIX9 was digested with ClaI, blunted with T4 polymerase and religated to create pAAV (Cla⁻)-CMV-FIX9.

The entire expression cassette containing HNF-3.albumin promoter-synthetic intron-hFVIII-synthetic poly A signal was excised from pZ8.I.dB.egg.A using NotI and ligated to the plasmid backbone and AAV ITRs from pAAV (Cla−)-CMV-FIX9 to create pAAV-F8-1. The nucleotide sequence of the vector from ITR to ITR (i.e., excluding plasmid backbone) is shown in SEQ ID NO 13.

EXAMPLE 3

Virion Production

AAV vectors were produced from these plasmids using the Ad free system as previously described in U.S. Pat. No. 5,858,351; U.S. Pat. No. 5,846,528; U.S. Pat. No. 5,622,856; and Matsushita et al., Gene Ther 5:938 (1998) all of which are hereby incorporated by reference. Briefly, 293 cells (ATCC, catalog number CRL-1573) were seeded in 10 cm dishes at a density of $3 \times 10^6$ cells per dish in 10 ml medium and incubated at 37° C. with $CO_2$ and humidity. After an overnight incubation, cells were approximately seventy to eighty percent confluent.

The cells were then transfected with DNA by the calcium phosphate method, as is well known in the art. Briefly, 7 µg of AAV vector containing the Factor VIII coding region, 7 µg of pladeno5 which supplies the accessory functions, and 7 µg of 1909 AAV helper were added to a 3 ml sterile, polystyrene snap cap tube using sterile pipette tips. Then, 1.0 ml of 300 mM $CaCl_2$ (JRH grade) was added to each tube and mixed by pipetting up and down. An equal volume of 2x HBS (274 mM NaCl, 10 mM KCl, 42 mM HEPES, 1.4 mM $Na_2PO_4$, 12 mM dextrose, pH 7.05, JRH grade) was added with a 2 ml pipette, and the solution was pipetted up and down three times. The DNA mixture was immediately added to the cells, one drop at a time, evenly throughout the 10 cm dish. The cells were then incubated at 37° C. with $CO_2$ and humidity for six hours. A granular precipitate was visible in the transfected cell cultures. After six hours, the DNA mixture was removed from the cells, which were provided with fresh medium and incubated for 72 hours.

After 72 hours, the cells were harvested, pelleted, and resuspended in 1 ml TBS/1% BSA. Freeze/thaw extracts were prepared by repeatedly (three times) freezing the cell suspension on dry ice and thawing at 37° C. Viral preps were stored at −80° C. and titered by dot blot assay prior to the first round of infection.

EXAMPLE 4

In Vitro Cell Transduction

Cells from the stable human cell line, 293 (ATCC No. CRL1573) were seeded in six-well plates (i.e., plates having six wells for cell growth) at a density of $5\times10^5$ cells/well. When the monolayers reached 80–90% confluence, they were infected with rAAV virions AAV-eδD-FVIII-HC, AAV-eδD-FVIII-LC, an equal ratio of AAV-eδD-FVIII-HC and AAV-eδD-FVIII-LC, or AAV-eδD-FIX at MOIs of $3\times10^3$ and $3\times10^4$. Eighteen hours post infection, the media were replaced with DMEM/10% heat inactivated FBS. The media were collected later for analysis by ELISA (as described below) for FVIII light chain antigen levels, and by the ChromZ FVIII as coagulation activity (FVIII-c) assay (Helena Labs) for biological activity, using the manufacturer's instructions and as described in Example 6.

EXAMPLE 5

Single Chain Factor VIII Infectivity Assay

In this Example, the infectivity of single chain Factor VIII was investigated. To determine the infectivity of rAAV-hF8-1, HepG2, 293, and H2.35 cells were infected with rAAV-hF8-1 and a control vector rAAV-hF8L at an MOI of $1\times10^4$ viral particles per cell. Recombinant AAV DNA in infected cells was isolated by Hirt extraction and run on an alkaline agarose gel. Southern blot analysis using an human F8 probe showed that similar amounts of rAAV-hF8-1 and rAAV-hF8L were isolated from uncoated virus in the infected cells. An infectious center assay (ICA) known in the art (See e.g., Snyder, *Current Protocols in Genetics,* Chapter 12, John Wiley & Sons [1997]) was used to further characterize the infectivity of rAAV-hF8-1. In this assay, the infectious particle to total particle ratio of rAAV-F8-1 and that of a control rAAV vector with the genome size of 4645 nucleotides was determined. The results indicated that rAAV-hF8-1 had an infectious particle to total particle ratio that was comparable to the control vector at approximately 1:1000. Taken together, these results indicate rAAV-hF8-1 has similar infectivity as rAAV vectors with the genome size of wild-type AAV.

EXAMPLE 6

Factor VIII Protein Expression Assay

An ELISA specific for the light chain of FVIII was used to determine FVIII light chain antigen levels in the 293 cells, as well as the injected animals (described below). NUNC Maxisorb 96 well plates were coated with 50 μl of a 1:500 dilution of the light chain specific antibody, N77110 (Biodesign International) in a coating buffer overnight at 4° C. The plate was washed three times with wash buffer (PBS, 0.05% Tween 20) and blocked with 200 μl blocking buffer (PBS, 10% horse serum, 0.05% Tween 20) at room temperature for 1 hour. The plate was washed three times and standards and samples were applied. Bioclate recombinant human FVIII (Baxter Hyland) was used as the standard, and was diluted in blocking buffer to concentrations ranging from 320 ng/ml to 10 ng/ml.

For analysis of transduced culture supernatants, the standards contained 50% media, and for analysis of mouse plasma, the standards were diluted into 10%, in normal pooled mouse plasma (Sigma). A standard assay reference plasma (SARP; Helena Labs) was also included in the assay. Following the loading of the standards and samples (95 μl/well), the plate was incubated at room temperature for 2 hours, and washed five times with wash buffer (200 μl/well). A 1:200 dilution of a horseradish peroxidase-conjugated light chain specific antibody, ESH8-HRP, (American Diagnostica) was added (100 μl/well), and the plate was incubated for 1 hour at room temperature. The plates were then washed four times with wash buffer, and the antigen was detected using an ABTS peroxidase substrate kit (BioRad) according to the manufacturer's instructions. The results are shown in Table 1 of Example 7, below.

EXAMPLE 7

Factor VIII Biological Activity Assay

The ChromZ FVIII coagulation activity (FVIII-c) assay (Helena Labs, Beaumont, Tex.) was used to detect biologically active FVIII in the 293 cells infected as described in Example 4. Bioclate recombinant human FVIII (Baxter Hyland) was used as a standard to analyze transfected culture supernatant. The standards were diluted in plasma dilution buffer (supplied in kit) in the range of 10 ng/ml to 0.313 ng/ml, and were made 2.5% in media. Because this assay can detect both human and murine FVIII activity, it was modified to deplete biologically active human Factor VIII in the mouse plasma. Mouse plasma was pre-incubated with an antibody specific for human FVIII prior to performing the assay. The difference in FVIII activity between the untreated plasma sample and the antibody treated sample represent the amount of biologically active human FVIII in the plasma. The standard used in the assay was normal pooled human plasma (FACT; obtained from George King Biomedical). Serial dilutions of FACT were made in FVIII deficient plasma from undiluted (200 ng/ml) to 6.25 ng/ml. The standards (10 μl) were incubated at 37° C. for 15 min., with or without the addition of 2 μl antibody N77110. Similarly, mouse plasma samples were diluted in FVIII deficient plasma and 10 μl of these diluted samples were incubated with or without 2 μl of N77110 at 37° C. for 15 min., and immediately placed on ice. Thus, all incubations with antibody were done in a background of 100% plasma. The antibody adsorbed and non-adsorbed FACT standards, as well as the mouse plasma samples were diluted 1:20 in plasma detection buffer provided in the ChromZ kit. Thus, the final concentration of the FACT standards used in the assay ranged from 10 ng/ml to 0.313 ng/ml.

Twenty five microliters of these dilutions were added to a chilled 96 well plate. With the plate on ice, 25 μl of FJXa reagent and 50 μl of FX were added, and the plate was incubated at 37° C. for 15 min. Substrate (50 μl) was added and the plate was incubated for an additional 3 min at 37° C. The reaction was stopped with the addition of 25 μl 50% acetic acid and the optical density at 405 nm was measured.

As shown below in Table 1, infection of 293 cells with AAV-eδD-FVIII-HC resulted in no antigen production, as well as no biologically-active protein. Cells infected with AAV-eδD-FVIII-LC produced FVIII light chain, but no biologically active protein. However, cells transduced with both vectors produced FVIII light chain and biologically active FVIII in a dose-dependent maimer. Transduction of cells with the negative control vector, AAV-eδD-FIX, resulted in no antigen nor any biologically active FVIII. It was assumed that equal amounts of heavy and light chains were produced in transduced cells. The activity units were converted to nanograms using the definition of one unit being equal to the amount of FVIII in 1 ml of normal pooled human plasma, or 200 ng.

TABLE 1

In Vitro Production of Biologically Active Human Factor VIII From Two rAAV Vectors

| Vector | MOI | ELISA (ng/ml) | ChromZ (mU/ml) | ChromZ (ng/ml) |
|---|---|---|---|---|
| AAV-eδD-FVIII-HC and AAV-eδD-FVIII-LC | $3 \times 10^3$ | 24 | 35 | 7.1 |
| AAV-eδD-FVIII-HC and AAV-eδD-FVIII-LC | $3 \times 10^4$ | 121 | 440 | 87.9 |
| AAV-eδD-FVIII-HC | $3 \times 10^3$ | 0 | 0 | 0 |
| AAV-eδD-FVIII-HC | $3 \times 10^4$ | 0 | 0 | 0 |
| AAV-eδD-FVIII-LC | $3 \times 10^3$ | 20.5 | 0 | 0 |
| AAV-eδD-FVIII-LC | $3 \times 10^4$ | 96.9 | 0 | 0 |
| AAV-hFIX | $3 \times 10^3$ | 0 | 0 | 0 |
| AAV-hFIX | $3 \times 10^4$ | 0 | 0 | 0 |
| No Vector | | 0 | 0 | 0 |

EXAMPLE 8

Immunofluorescent Staining of FVIII Heavy and Light Chains

In these experiments, 293 cells transduced as described above were analyzed using immunofluorescent staining. 293 cells were plated on rat tail collagen-coated two-well culture slides at a density of $4 \times 10^5$ cells per well. Forty-eight hours later, the cells were transduced at an MOI of $3 \times 10^4$ particles per cell of rAAV-hFVIII-HC and rAAV-hFVIII-LC. Forty-eight hours post-transduction, the cells were fixed in situ with acetone, blocked with 2% BSA, and stained with a fluorescently labelled anti-hFVIII light chain antibody and a fluorescently labelled anti-hFVIII heavy chain antibody. The anti-hFVIII light chain antibody used was ESH-4 monoclonal antibody (American Diagnostica), fluorescently labelled with alexa-488 (Molecular Probes), according to the manufacturer's instructions. The anti-hFVIII heavy chain antibody used was MAS530P monoclonal antibody (Accurate Chemical) fluorescently labelled with alexa-594 (Molecular Probes), according to the manufacturer's instructions. The cells were counter-stained with DAPI. The images were collected using a Zeiss Axioskop fluorescence microscope equipped with separate filters for DAPI, FITC, and rhodamine signals and a CCD camera. Image analysis was performed using Quips imaging software (Vysis).

As indicated above, infection of cells with either rAAV-eδD-FVIII-HC or AAV-eδD-FVIII-LC, followed by staining with antibodies to both chains resulted in production of the individual chains of human FVIII. Immunofluorescent staining of cells co-infected with both vectors demonstrated that although some cells express only the heavy or light chain of hFVIII, many co-expressed both chains of human FVIII.

EXAMPLE 9

In Vitro Expression of Factor VIII Using Single Construct

Table 2 shows that two single vector constructs containing the heavy and the light chain of Factor VIII driven by different promoters express biologically active Factor VIII. The constructs pAAV-hF8-1 (SEQ ID NO:13) and pVm4.1cF8ΔB (SEQ ID NO:14) were transfected into 293 cells. Following transfection, the cells were allowed to express factor VIII for 48–72 hours. Factor VIII in the culture media was assayed by the ChromZ FVIII coagulation activity (FVIII-c) assay, as per the manufacturer's instructions.

TABLE 2

In Vitro Production of Biologically Active FVIII

| Construct(s) | ELISA (ng/ml) | ChromZ (ng/ml) |
|---|---|---|
| Control | — | 0 |
| pAAV-hF8-1 | — | 4.9 |
| pVm4.1cF8ΔB | — | 46 |

EXAMPLE 10

Factor VIII Expression Using Tissue Specific Promoters

In these experiments, different promoters and enhancer elements were used to drive expression of a Factor VII coding sequence. Expression of Factor VIII was compared in 293 cells and HepG2 cells using different promoters. The pAAVeF8ΔB contains an EF-1α promoter with a hGH intron, Factor VIII with a B-domain deletion (F8ΔB) and a polyA. As described previously, pAAV-hF8-1 uses the HNF-3 albumin promoter with a minimal intron followed by F8ΔB and a minimal polyA. The construct pAAV-c8 uses the CMV enhancer-promoter and the F8ΔB. pAAV8b1 contains the HNF-3 albumin promoter followed by the CMV/B-globin intron with the F8ΔB and a minimal polyA site. Table 3 describes Factor VIII expression using the albumin promoter relative to the control plasmid pV4.1eF8ΔB in HepG2 and 293 cells. These data show increased expression of Factor VIII in HepG2 liver cells with the albumin promoter as compared to Factor VIII expression in 293 cells.

TABLE 3

Relative Tissue Specificity of Promoters

| Plasmid Construct | HepG2 Cells | 293 Cells |
|---|---|---|
| pAAV-hF8-1 | 6.2 | 0.6 |
| pAAV8b1 | 6.7 | 1.0 |
| pAAVc8 | 30.0 | 41.0 |
| pV4.1eF8ΔB | 100 | 100 |

Next, several promoters derived from the transthyretin (TTR) gene promoter were transfected into HepG2 cells. TTR is an abundant serum protein and the gene enhancer-promoter contains well known liver-specific transcription factor binding sites (Samadani et al., Gene Expression 6:23 [1996]; Yan et al., EMBO 9:869 [1990]; Costa and Grayson, Nuc. Acids Res., 19:4139 [1991]; Costa et al, Mol. Cell. Bio., 6:4697 [1986]). The constructs were made by replacing the HNF-3 albumin promoter in pAAV-hF8-1 with various lengths of the TTR promoter-enhancer. The TTR enhancer-promoter was modified by replacing the weak affinity binding sites with the strong affinity binding sites to create pAAV-hF8-2. The pAAV-hF8-TTR-E-L-P202 construct contains the full TTR promoter with a linker between the enhancer and the promoter. The remaining constructs are 5' deletions: pAAV-hF8-TTR-E-P202 has the promoter and enhancer with no linker; pAAV-hF8-TTR-E-P197 has a 5 base pair deletion from the promoter; pAAV-hF8-TTR-E-P151 has a 50 base pair deletion; pAAV-hF8-TTR-P202 lacks the TTR enhancer and pAAV-hF8-TTR(X) has a 65 base pair deletion in the enhancer. The control plasmid, pAAV-hF8-1, expressed approximately 4.6 mU/ml. Table 4 shows the fold-increase in Factor VIII activity using the TTR promoter series relative to the control plasmid.

TABLE 4

Factor VIII Expression Using TTR-Derived Promoters

| Plasmid Construct | Relative Factor VII Activity |
|---|---|
| pAAV-hF8-STTR | 3.16 |
| pAAV-hF8-TTR-E-L-P202 | 8.86 |
| pAAV-hF8-TTR-E-P202 | 6.1 |
| pAAV-hF8-TTR-EP197 | 7.3 |
| pAAV-hF8-TTR-E-P151 | 13.3 |
| pAAV-hF8-TTR-P202 | 2.3 |

EXAMPLE 11

In Vivo Expression of Factor VIII

In order to test the feasibility of the AAV vector approach of the present invention in vivo, three groups of five C57BL/6 mice were injected via the portal vein with either $3\times10^{11}$ particles of AAV-eδD-FVIII-HC, $3\times10^{11}$ particles of AAV-eδD-FVIII-LC, or $3\times10^{11}$ particles of both AAV-eδD-FVIII-HC and AAV-eδD-FVIII-LC. In addition, a group of four animals was injected with $3\times10^{11}$ particles of AAV-eδD-FIX. It has been shown that this strain of mice does not elicit an immune response to human FVIII when the gene is delivered to the liver via an adenoviral vector (Connelly et al., Blood 87:4671–4677 [1996]). As indicated by the results shown below, the data obtained during these experiments demonstrate the feasibility of producing biologically active FVIII using two AAV vectors to independently deliver the heavy and light chains of FVIII.

Figure 8:
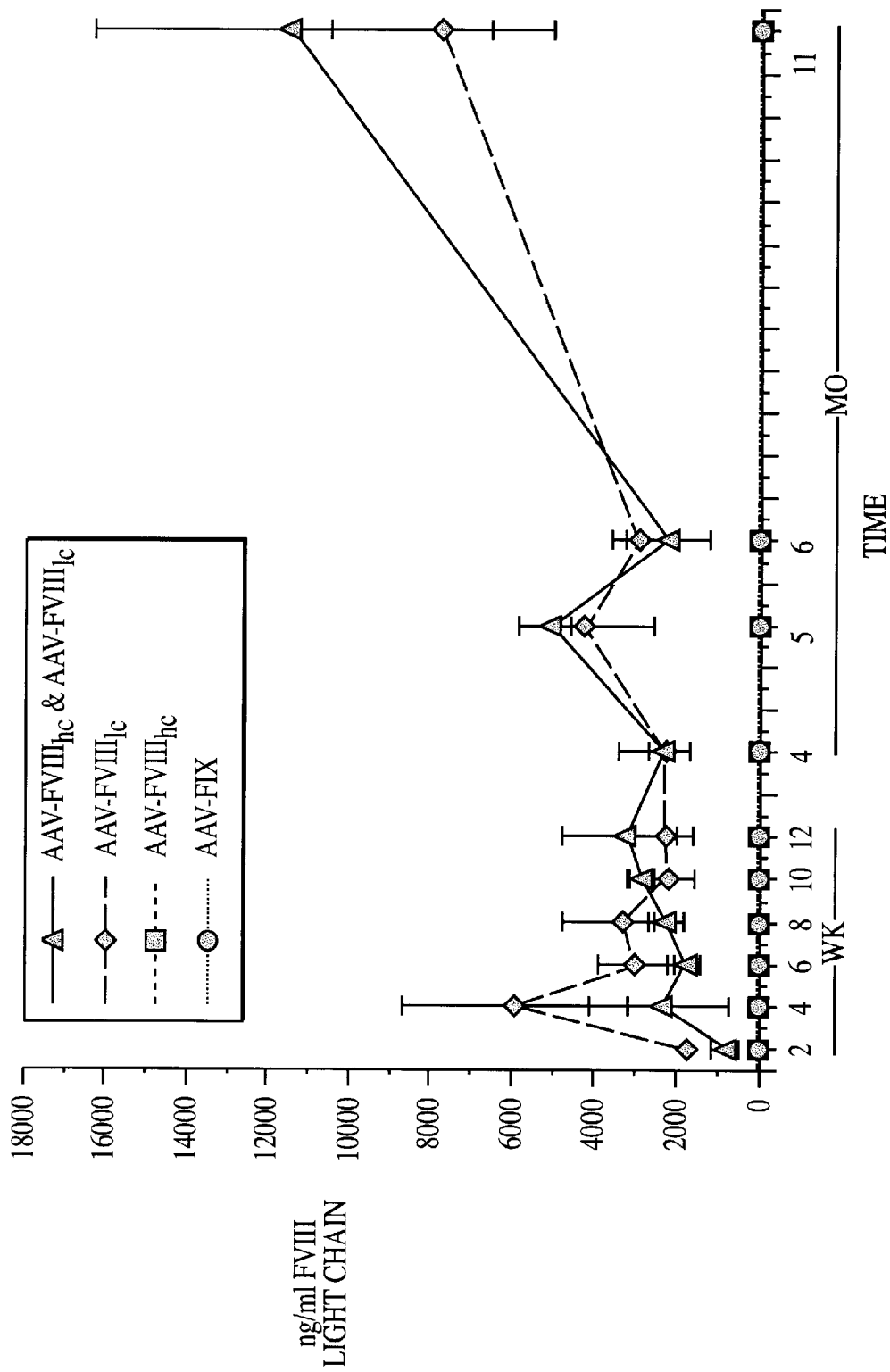
FIG. 8 provides a graph demonstrating the expression of various human FVIII constructs in mouse plasma.

Blood samples were collected in sodium citrate via the retro-orbital plexus at biweekly intervals for the first 2 months and at monthly intervals thereafter for 6 months and at 11 months. Very high levels of FVIII light chain were expressed in animals injected with AAV-eδD-FVIII-LC alone or both vectors as shown in FIG. 8.

In order to assess the amount of biologically active human FVIII produced in the animals, a modified ChromZ assay was used. Since this assay detects both human and murine FVIII, the amount of FVIII present in the plasma before and after adsorption to an antibody specific to human FVIII was determined. The amount of FVIII remaining in the plasma after adsorption represented the amount of active murine FVIII and the difference represented the amount of active human FVIII. Control experiments demonstrated that the antibody could remove 80–90% of the human FVIII from a mouse plasma sample when the sample was spiked with up to 32 ng of human FVIII. The modified ChromZ assay indicated that only those animals injected with both vectors produced biologically active FVIII, as indicated in Table 5. The results shown in Table 5 are those from plasma collected 8 weeks post-injection, although similar results were obtained at 10 weeks and 5 months post-injection. One of the five animals co-injected with both the heavy and light chain vector did not express VIII, presumably due to an inefficient injection, and was omitted from the analysis. Animals injected with both vectors produced over 2 gg/ml hFVIII light chain as measured by ELISA. The ChromZ assay indicated that a total of 600–900 ng/ml of active hFVIII was detected in the plasma. The contribution from murine Factor VIII was approximately 400–500 ng/ml, indicating that about 230–430 ng/ml of active human Factor VIII was present in the plasma. Although only a fraction of the total protein was found to be active, the animals produced physiological levels of the active protein (i.e., 200 ng/ml). The animals were found to have maintained these physiological levels of active protein for more than 11 months, without waning. Similar analyses preformed on animals injected with the light chain vector alone, the heavy chain vector alone, or the hFIX vector demonstrated no biologically active human FVIII in the plasma of these animals.

TABLE 5

Biological Activity of Human Factor VIII In Vivo

| Construct(s) Used | ELISA (ng/ml) | Total FVIII (−Ab) (Units) | Murine FVIII (+Ab) (Units) | Human FVIII (ng/ml) |
|---|---|---|---|---|
| AAV-eδD-FVIII-HC and AAV-eδD-FVIII-LC* | 2288 | 3.9 | 2.2 | 342 |
| AAV-eδD-FVIII-LC* | 3329 | 1.4 | 1.6 | 0 |
| AAV-eδD-FVIII-HC | 0 | 1.6 | 1.6 | 0 |
| AAV-eδD-FIX | 0 | 1.4 | 2.0 | 0 |

*Average of three animals.

EXAMPLE 12

Gene Transfer and Vector Expression in Tissues

In these experiments, evidence of gene transfer to liver was obtained by Southern Blot analysis following isolation of DNA from one animal of each experimental group sacrificed 8 weeks post-injection (i.e., as described in Example 11). In addition, DNA was obtained from other tissues in order to determine the degree of vector expression in organs other than the liver.

Twenty micrograms of DNA was digested with BglII, separated using a 1% agarose gel, and hybridized with a $^{32}$P-labelled 1126 bp AlwNI fragment encoding the A1 and A2 domains of HFVIII (heavy chain probe), or a $^{32}$P-labelled 1456 bp NdeI-EcoRI fragment encoding the A3, C1 an C2 domains of hFVIII (light chain probe). Copy number controls were generated by spiking Bg/II-digested naive mouse liver DNA with BlgII-digested heavy or light chain plasmid DNA (pVm4.1eδD-hFVIII-HC and pVm41.eδD-hFVIII-LC, respectively), at ratios of 10, 5, 1, 01, and 0.01 copies per diploid genome. The hybridized membranes were analyzed using a Storm 860 phosphoimager (Molecular Dynamics), and quantitation of vector copy number was evaluated using ImageQuaNT software (Molecular Dynamics). Autoradiography of the hybridized membranes was also performed. Total RNA was isolated from liver tissue using the RNA Stat extraction kit (Tel-Test). As describe briefly below, Northern blot analysis was also performed on 10 μg RNA using methods known in the art, in conjunction with the $^{32}$P-labelled probes specific to the heavy and light chains of hFVIII described above and autoradiography was performed on the hybridized membranes.

Figure 9A:
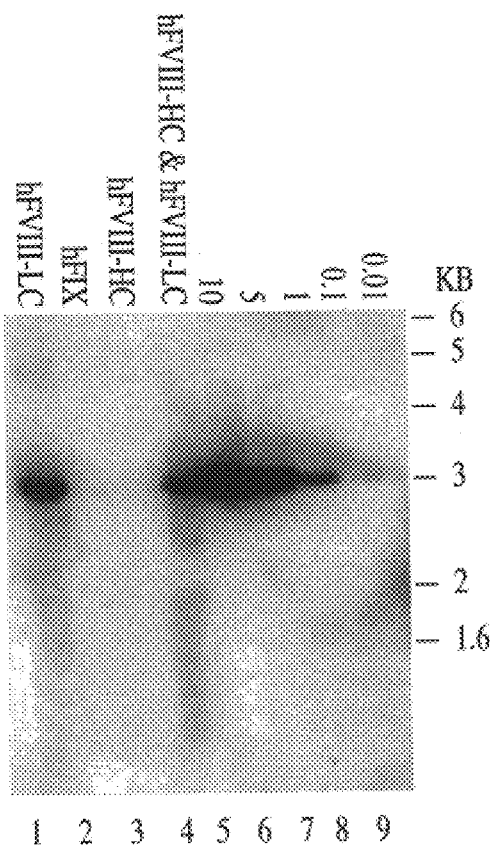
FIGS. 9A–B provides Southern blot analyses of liver DNA using probes specific for (A) the light chain of hFVIII, and (B) the heavy chain of hFVIII.
Figure 9B:
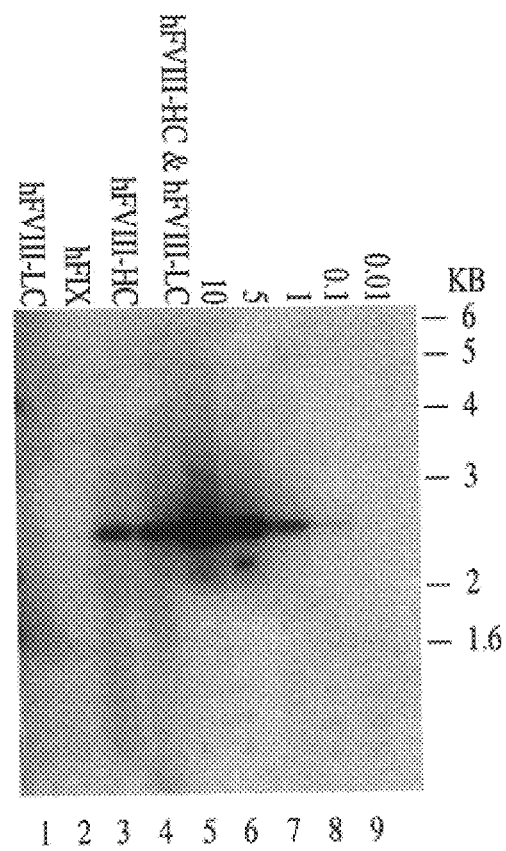

Following digestion of liver DNA with BgII and hybridization with an hFVIII light chain probe described below, using methods known in the art, a band at the predicted size of 3015 bp was detected in animals injected with rAAV-hFVIII-LC, or both the heavy and light chain vectors. This band was not observed in the DNA of animals injected with the heavy chain vector alone or the hFIX vector, as shown in FIG. 9A (rAAV-hFVIII-LC, lane 1; rAAV-hFIX, lane 2; rAAV-hFVIII-HC, lane 3; both rAAV-hFVIII-LC and rAAV-hFVIII-HC, lane 4; copy number controls were generated by spiking BglII digested naive mouse liver DNA with the corresponding plasmids at ratios of 10, 5, 1, 0.1, and 0.01 copies per diploid genome, lanes 5–9). Phosphoimage analysis revealed that the light chain vector was present at approximately 2.4 and 1.5 copies per diploid genome in animals injected with the light chain vector alone or both vectors, respectively. When BgII-digested DNA was hybridized with an hFVIII heavy chain probe, the expected band of 2318 bp was observed in animals injected with the heavy chain vector alone or both vectors, but was not detected in animals injected with the light chain vector alone or the HFIX vector, as shown in FIG. 9B. The copy number in animals injected with the heavy chain vector alone and both vectors was 1.1 and 1.7 vector copies per diploid genome, respectively.

Figure 10A:
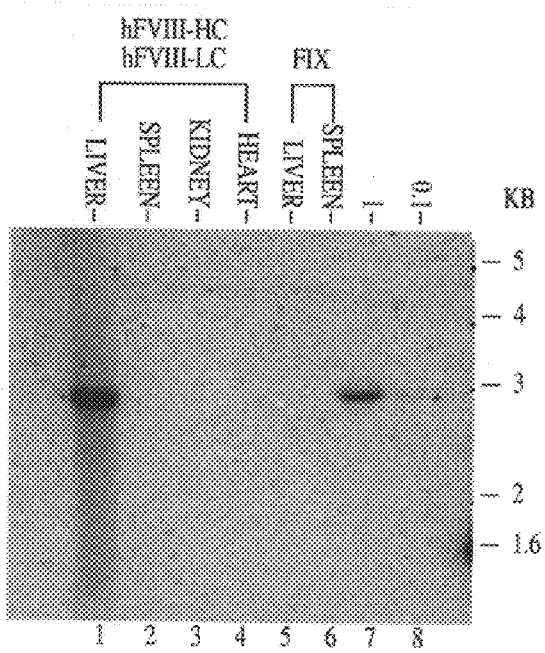
FIGS. 10A–B provides Southern blot analyses of DNA from different tissues using probes specific for (A) the light chain of hFVIII, and (B) the heavy chain of hFVIII.
Figure 10B:
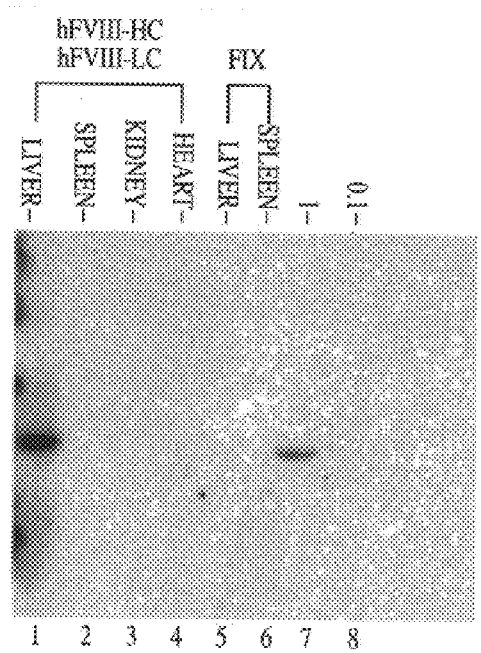

The results of hybridization of DNA extracted from the spleen, kidney and heart tissue with either an hFVIII light chain probe or a heavy chain probe indicated that these tissues contained less than I copy of vector sequences per 10 diploid genomes, demonstrating that the vector distributes primarily to the liver following intra-portal injection, as shown in FIGS. 10A and 10B.

Figure 11A:
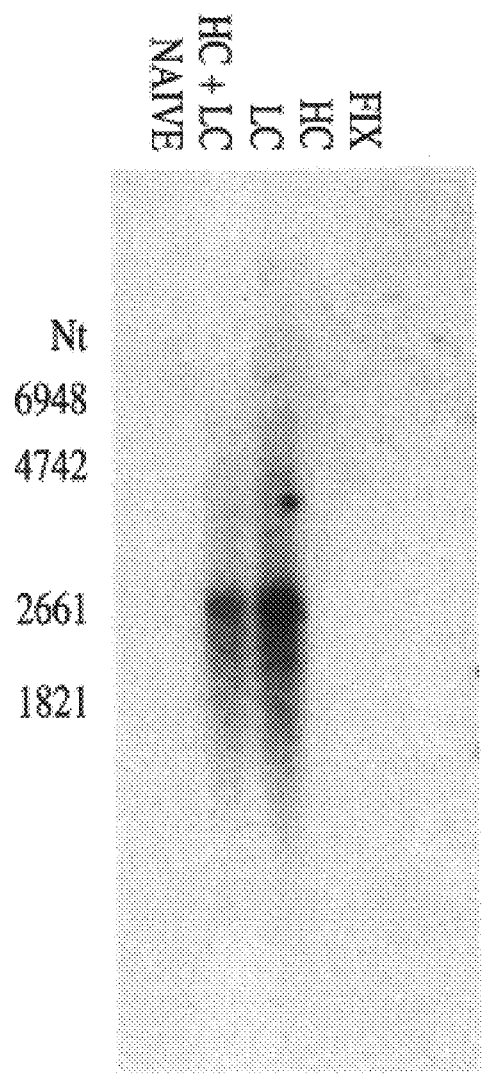
FIGS. 11A–B provides Northern blot analyses of liver RNA using probes specific for (A) the light chain of hFVIII, and (B) the heavy chain of hFVIII.
Figure 11B:
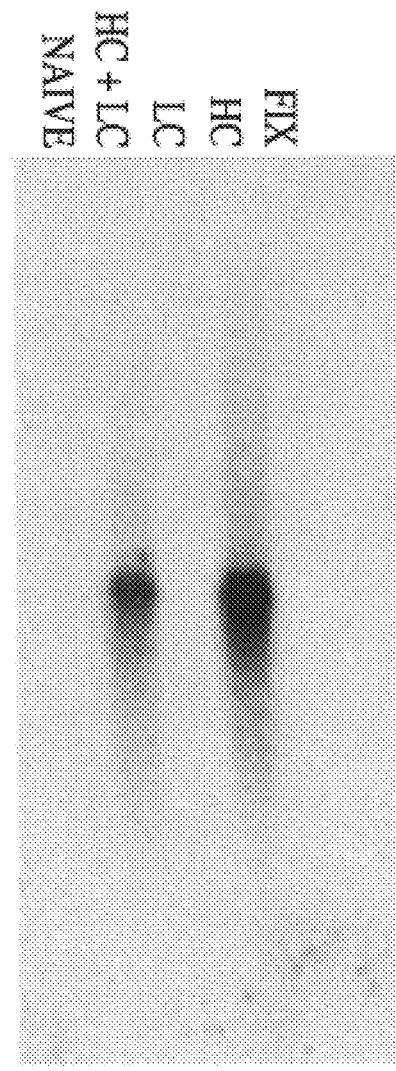

Human FVIII gene expression in the liver of the mice was also assessed by Northern blot analysis on RNA isolated from animals sacrificed 8 weeks post-injection (as described above). hFVIII light chain transcripts of the predicted size (2.7 kb) were observed in animals injected with the light chain vector alone or both vectors, as shown in FIG. 11A. Similarly, the expected hFVIII heavy chain transcripts (2.7 kb) were detected in animals that were injected with the heavy chain vector alone or both vectors, as shown in FIG. 11B. Since the heavy and light chain DNA sequences were shown by Southern blot analysis to be present at approximately the same copy number (1.7 and 1.5 copies per diploid genome, respectively), in an animal injected with both vectors, these results demonstrate that both the heavy and light chains of hFVIII are expressed in the liver in approximately equivalent amounts.

EXAMPLE 13

In Vivo Expression of Factor VIII Using Single Vectors

Several groups comprising four C57BL/6 mice were injected via the portal vein with $3 \times 10^{11}$ particles of AAV-hF8-STTR, $3 \times 10^{11}$ particles of AAV-hF8-hAAT-137, or $3 \times 10^{11}$ particles of AAV-hF8-HNF3-alb-original. As discussed above, AAV-hF8-STTR contains modified sequences from the transthyretin gene promoter. AAV-hF8-hAAT-137 contains 137 base pairs of the human,-antitrypsin promoter. See De Simone et al., EMBO J., 6:2759–2766 (1987). AAV-hF8-HNF3-alb-original, like AAV-F8-1, contains three HNF3 binding sites and 54 base pairs of the albumin promoter.

Expression of Factor VIII was measured at 4 weeks by human Factor VIII-specific ELISA (Affinity Biologicals). Even at this early time-point, several of these mice expressed between 2 and 20 ng/ml of human Factor VIII. Table 6 shows expression levels at 4 weeks post-infection for selected animals.

TABLE 6

Factor VIII Expression at 4 Weeks

| rAAV | Factor VIII Levels (ng/ml) |
|---|---|
| rAAV-hF8-STTR (mouse #1) | 4.3 |
| rAAV-hF8-STTR (mouse #2) | 2.4 |
| rAAV-hF8-hAAT-137 (mouse #1) | 10.5 |
| rAAV-hF8-hAAT-137 (mouse #2) | 20.4 |
| rAAV-hF8-HNF3-alb-original (mouse #1) | 2.2 | rAAV-hF8-hAAT-137 produced expression levels of as much as 10 to 20 ng/ml, which represent 20% to 40% of normal human levels of Factor VIII. These data therefore show the in vivo expression of therapeutically effective amounts of human Factor VIII using single factor AAV vectors.

We claim:

1. A method of treating hemophilia in a mammal, comprising:
   a. providing recombinant adeno-associated virus virions comprising a nucleotide sequence encoding Factor VIII operably linked to expression control elements; and
   b. administering said recombinant adeno-associated virus virions to a mammal under conditions that result in the expression of Factor VIII protein at a level that provides a therapeutic effect in said mammal.

2. The method of claim 1, wherein said Factor VIII protein is expressed in the liver.

3. The method of claim 1, wherein said recombinant adeno-associated virus virions are administered to the liver.

4. The method of claim 1, wherein said expression control elements comprise a tissue-specific promoter.

5. The method of claim 4, wherein said expression control elements comprise a liver-specific promoter.

6. The method of claim 1, wherein said expression control elements comprise a human growth hormone polyadenylation sequence.

7. The method of claim 1, wherein said recombinant adeno-associated virus virions are administered via intravenous administration.

8. The method of claim 7, wherein said intravenous administration is via the portal vein.

9. The method of claim 1, wherein said recombinant adeno-associated virus virions are administered via intraarterial administration.

10. The method of claim 9, wherein said recombinant adeno-associated virus virions are administered via the hepatic artery.

11. The method of claim 1, wherein said nucleotide sequence encoding Factor VIII comprises a light chain and a heavy chain and wherein said light chain and heavy chain are operably linked by a junction.

12. The method of claim 11, wherein said nucleotide sequence is SEQ ID 13, such that said junction has the amino acid sequence Ser-Phe.

13. The method of claim 11, wherein said nucleotide sequence is SEQ ID 14, such that said junction has the amino acid sequence Ser-Phe-Ser-Gln-Asn-Pro-Pro-Val-Leu-Lys-Arg-His-Gln-Arg.

14. The method of claim 11, wherein said expression control elements comprise a liver-specific promoter, and wherein said recombinant adeno-associated virus virions are administered to the liver of said mammal.

15. The method of claim 13, wherein said expression control elements comprise a liver-specific promoter, and wherein said recombinant adeno-associated virus virions are administered to the liver of said mammal.

16. A method of treating hemophilia in a mammal, said method comprising:
   a. providing a first recombinant adeno-associated virus virion comprising a nucleotide sequence encoding the light chain of Factor VIII operably linked to expression control elements; and
   b. providing a second recombinant adeno-associated virus virion comprising a nucleotide sequence encoding the heavy chain of Factor VIII operably linked to expression control elements; and
   c. administering said first and second recombinant adeno-associated virus virions to a mammal under conditions that result in the expression of Factor VIII protein at a level that provides a therapeutic effect in said mammal.

17. The method of claim 16, wherein said Factor VIII protein is expressed in the liver.

18. The method of claim 16, wherein said recombinant adeno-associated virus virions are administered to the liver.

19. The method of claim 16, wherein said expression control elements comprise a tissue-specific promoter.

20. The method of claim 19, wherein said expression control elements comprise a liver-specific promoter.

21. The method of claim 16, wherein said expression control elements comprise a human growth hormone polyadenylation sequence.

22. The method of claim 16, wherein said recombinant adeno-associated virus virions are administered via intravenous administration.

23. The method of claim 22, wherein said intravenous administration is via the portal vein.

24. The method of claim 16, wherein said recombinant adeno-associated virus virions are administered via intraarterial administration.

25. The method of claim 24, wherein said recombinant adeno-associated virus virions are administered via the hepatic artery.

* * * * *

SEQUENCE LISTING

<160> NUMBER OF SEQ ID NOS: 15

<210> SEQ ID NO 1
<211> LENGTH: 59
<212> TYPE: DNA
<213> ORGANISM: Artificial Sequence
<220> FEATURE:
<223> OTHER INFORMATION: Description of Artificial Sequence: Synthetic

<400> SEQUENCE: 1
cccaagcttg cggccgcccg ggtgccgccc ctaggcaggt aagtgccgtg tgtggttcc      59

<210> SEQ ID NO 2
<211> LENGTH: 59
<212> TYPE: DNA
<213> ORGANISM: Artificial Sequence
<220> FEATURE:
<223> OTHER INFORMATION: Description of Artificial Sequence: Synthetic

<400> SEQUENCE: 2

-continued ccgctcgagc agagctctat ttgcatggtg aatcgatgc cgcgggaacc acacacggc    59

<210> SEQ ID NO 3
<211> LENGTH: 103
<212> TYPE: DNA
<213> ORGANISM: Artificial Sequence
<220> FEATURE:
<223> OTHER INFORMATION: Description of Artificial Sequence: Synthetic

<400> SEQUENCE: 3
cccaagcttg cggccgcccg ggtgccgccc ctaggcaggt aagtgccgtg tgtggttccc    60
gcggcatcga ttccaccatg caaatagagc tctgctcgag cgg                    103

<210> SEQ ID NO 4
<211> LENGTH: 57
<212> TYPE: DNA
<213> ORGANISM: Artificial Sequence
<220> FEATURE:
<223> OTHER INFORMATION: Description of Artificial Sequence: Synthetic

<400> SEQUENCE: 4
ttcccgcggg cctggcctct ttacgggtta tggcccttgc gtgccttgaa ttactga      57

<210> SEQ ID NO 5
<211> LENGTH: 57
<212> TYPE: DNA
<213> ORGANISM: Artificial Sequence
<220> FEATURE:
<223> OTHER INFORMATION: Description of Artificial Sequence: Synthetic

<400> SEQUENCE: 5
gaatcgatac ctgtggagaa aagaaaaag tggatgtcag tgtcagtaat tcaaggc       57

<210> SEQ ID NO 6
<211> LENGTH: 99
<212> TYPE: DNA
<213> ORGANISM: Artificial Sequence
<220> FEATURE:
<223> OTHER INFORMATION: Description of Artificial Sequence: Synthetic

<400> SEQUENCE: 6
ttcccgcggg cctggcctct ttacgggtta tggcccttgc gtgccttgaa ttactgacac   60
tgacatccac tttttctttt tctccacagg tatcgattc                          99

<210> SEQ ID NO 7
<211> LENGTH: 100
<212> TYPE: DNA
<213> ORGANISM: Artificial Sequence
<220> FEATURE:
<223> OTHER INFORMATION: Description of Artificial Sequence: Synthetic

<400> SEQUENCE: 7
agggaatgtt tgttcttaaa taccatccag ggaatgtttg ttcttaaata ccatccaggg   60
aatgtttgtt cttaaatacc atctacagtt attggttaaa                         100

<210> SEQ ID NO 8
<211> LENGTH: 59
<212> TYPE: DNA
<213> ORGANISM: Artificial Sequence
<220> FEATURE:
<223> OTHER INFORMATION: Description of Artificial Sequence: Synthetic

<400> SEQUENCE: 8
ggaaaggtga tctgtgtgca gaaagactcg ctctaatata cttctttaac caataactg    59

<210> SEQ ID NO 9
<211> LENGTH: 144
<212> TYPE: DNA
<213> ORGANISM: Artificial Sequence
<220> FEATURE:
<223> OTHER INFORMATION: Description of Artificial Sequence: Synthetic

<400> SEQUENCE: 9
agggaatgtt tgttcttaaa taccatccag ggaatgtttg ttcttaaata ccatccaggg      60
aatgtttgtt cttaaatacc atctacagtt attggttaaa aagtatatt agagcgagtc     120 tttctgcaca cagatcacct ttcc                                            144

<210> SEQ ID NO 10
<211> LENGTH: 59
<212> TYPE: DNA
<213> ORGANISM: Artificial Sequence
<220> FEATURE:
<223> OTHER INFORMATION: Description of Artificial Sequence: Synthetic

<400> SEQUENCE: 10
tcgagaataa aagatcagag ctctagagat ctgtgtgttg gttttttgtg tgcggccgc       59

<210> SEQ ID NO 11
<211> LENGTH: 59
<212> TYPE: DNA
<213> ORGANISM: Artificial Sequence
<220> FEATURE:
<223> OTHER INFORMATION: Description of Artificial Sequence: Synthetic

<400> SEQUENCE: 11
tcgagcggcc gcacacaaaa aaccaacaca cagatctcta gagctctgat cttttattc       59

<210> SEQ ID NO 12
<211> LENGTH: 63
<212> TYPE: DNA
<213> ORGANISM: Artificial Sequence
<220> FEATURE:
<223> OTHER INFORMATION: Description of Artificial Sequence: Synthetic

<400> SEQUENCE: 12
tcgagaataa aagatcagag ctctagagat ctgtgtgttg gttttttgtg tgcggccgct      60
cga                                                                   63

<210> SEQ ID NO 13
<211> LENGTH: 11933
<212> TYPE: DNA
<213> ORGANISM: Artificial Sequence
<220> FEATURE:
<223> OTHER INFORMATION: Description of Artificial Sequence: Synthetic

<400> SEQUENCE: 13
cagctgcgcg ctcgctcgct cactgaggcc gcccgggcaa agcccggcg tcgggcgacc       60 tttggtcgcc cggcctcagt gagcgagcga gcgcgcagag agggagtggc caactccatc     120 actagggtt cctgcggccg cccagggaat gtttgttctt aaataccatc agggaatgt       180 ttgttcttaa ataccatcca gggaatgttt gttcttaaat accatctaca gttattggtt    240
aaagaagtat attagagcga gtctttctgc acacagatca cctttccggg tgccgcccct    300
aggcaggtaa gtgccgtgtg tggttcccgc gggcctggcc tctttacggg ttatggccct    360
tgcgtgcctt gaattactga cactgacatc cactttttct ttttctccac aggtatcgat    420

-continued

| | | | | | |
|---|---|---|---|---|---|
| tccaccatgc | aaatagagct | ctccacctgc | ttctttctgt | gccttttgcg | attctgcttt | 480 |
| agtgccacca | gaagatacta | cctgggtgca | gtggaactgt | catgggacta | tatgcaaagt | 540 |
| gatctcggtg | agctgcctgt | ggacgcaaga | tttcctccta | gagtgccaaa | atcttttcca | 600 |
| ttcaacacct | cagtcgtgta | caaaaagact | ctgtttgtag | aattcacgga | tcaccttttc | 660 |
| aacatcgcta | agccaaggcc | accctggatg | ggtctgctag | gtcctaccat | ccaggctgag | 720 |
| gtttatgata | cagtggtcat | tacacttaag | aacatggctt | cccatcctgt | cagtcttcat | 780 |
| gctgttggtg | tatcctactg | gaaagcttct | gagggagctg | aatatgatga | tcagaccagt | 840 |
| caaagggaga | agaagatga | taaagtcttc | cctggtggaa | gccatacata | tgtctggcag | 900 |
| gtcctgaaag | agaatggtcc | aatggcctct | gacccactgt | gccttaccta | ctcatatctt | 960 |
| tctcatgtgg | acctggtaaa | agacttgaat | tcaggcctca | ttggagccct | actagtatgt | 1020 |
| agagaaggga | gtctggccaa | ggaaaagaca | cagaccttgc | acaaatttat | actacttttt | 1080 |
| gctgtatttg | atgaagggaa | aagttggcac | tcagaaacaa | agaactcctt | gatgcaggat | 1140 |
| agggatgctg | catctgctcg | ggcctggcct | aaaatgcaca | cagtcaatgg | ttatgtaaac | 1200 |
| aggtctctgc | caggtctgat | tggatgccac | aggaaatcag | tctattggca | tgtgattgga | 1260 |
| atgggcacca | ctcctgaagt | gcactcaata | ttcctcgaag | gtcacacatt | tcttgtgagg | 1320 |
| aaccatcgcc | aggcgtcctt | ggaaatctcg | ccaataactt | tccttactgc | tcaaacactc | 1380 |
| ttgatggacc | ttggacagtt | tctactgttt | tgtcatatct | cttcccacca | acatgatggc | 1440 |
| atggaagctt | atgtcaaagt | agacagctgt | ccagaggaac | cccaactacg | aatgaaaaat | 1500 |
| aatgaagaag | cggaagacta | tgatgatgat | cttactgatt | ctgaaatgga | tgtggtcagg | 1560 |
| tttgatgatg | acaactctcc | ttcctttatc | caaattcgct | cagttgccaa | gaagcatcct | 1620 |
| aaaacttggg | tacattacat | tgctgctgaa | gaggaggact | gggactatgc | tcccttagtc | 1680 |
| ctcgcccccg | atgacagaag | ttataaaagt | caatatttga | acaatggccc | tcagcggatt | 1740 |
| ggtaggaagt | acaaaaaagt | ccgatttatg | gcatacacag | atgaaacctt | taagactcgt | 1800 |
| gaagctattc | agcatgaatc | aggaatcttg | ggacctttac | tttatgggga | agttggagac | 1860 |
| acactgttga | ttatatttaa | gaatcaagca | agcagaccat | ataacatcta | ccctcacgga | 1920 |
| atcactgatg | tccgtccttt | gtattcaagg | agattaccaa | aagtgtaaa | acatttgaag | 1980 |
| gattttccaa | ttctgccagg | agaaatattc | aaatataaat | ggacagtgac | tgtagaagat | 2040 |
| gggccaacta | aatcagatcc | tcggtgcctg | acccgctatt | actctagttt | cgttaatatg | 2100 |
| gagagagatc | tagcttcagg | actcattggc | cctctcctca | tctgctacaa | agaatctgta | 2160 |
| gatcaaagag | gaaaccagat | aatgtcagac | aagaggaatg | tcatcctgtt | ttctgtatttt | 2220 |
| gatgagaacc | gaagctggta | cctcacagag | aatatacaac | gctttctccc | caatccagct | 2280 |
| ggagtgcagc | ttgaggatcc | agagttccaa | gcctccaaca | tcatgcacag | catcaatggc | 2340 |
| tatgtttttg | atagtttgca | gttgtcagtt | tgtttgcatg | aggtggcata | ctggtacatt | 2400 |
| ctaagcattg | gagcacagac | tgacttcctt | tctgtcttct | tctctggata | taccttcaaa | 2460 |
| cacaaaatgg | tctatgaaga | cacactcacc | ctattcccat | tctcaggaga | aactgtcttc | 2520 |
| atgtcgatgg | aaaacccagg | tctatggatt | ctggggtgcc | acaactcaga | ctttcggaac | 2580 |
| agaggcatga | ccgccttact | gaaggtttct | agttgtgaca | agaacactgg | tgattattac | 2640 |
| gaggacagtt | atgaagatat | ttcagcatac | ttgctgagta | aaaacaatgc | cattgaacca | 2700 |
| agaagcttcg | aaataactcg | tactactctt | cagtcagatc | aagaggaaat | tgactatgat | 2760 |
| gataccatat | cagttgaaat | gaagaaggaa | gattttgaca | tttatgatga | ggatgaaaat | 2820 |

-continued

```
cagagccccc gcagctttca aaagaaaaca cgacactatt ttattgctgc agtggagagg    2880
ctctgggatt atgggatgag tagctcccca catgttctaa gaaacagggc tcagagtggc    2940
agtgtccctc agttcaagaa agttgttttc caggaattta ctgatggctc ctttactcag    3000
cccttatacc gtggagaact aaatgaacat ttgggactcc tggggccata tataagagca    3060
gaagttgaag ataatatcat ggtaactttc agaaatcagg cctctcgtcc ctattccttc    3120
tattctagcc ttatttctta tgaggaagat cagaggcaag gagcagaacc tagaaaaaac    3180
tttgtcaagc ctaatgaaac caaaacttac ttttggaaag tgcaacatca tatggcaccc    3240
actaaagatg agtttgactg caaagcctgg gcttatttct ctgatgttga cctggaaaaa    3300
gatgtgcact caggcctgat tggacccctt ctggtctgcc acactaacac actgaacct    3360 gctcatggga gacaagtgac agtacaggaa tttgctctgt ttttcaccat ctttgatgag    3420
accaaaagct ggtacttcac tgaaaatatg gaaagaaact gcagggctcc ctgcaatatc    3480
cagatggaag atcccacttt taaagagaat tatcgcttcc atgcaatcaa tggctacata    3540
atggatacac tacctggctt agtaatggct caggatcaaa ggattcgatg gtatctgctc    3600
agcatgggca gcaatgaaaa catccattct attcatttca gtggacatgt gttcactgta    3660
cgaaaaaaag aggagtataa aatggcactg tacaatctct atccaggtgt ttttgagaca    3720
gtggaaatgt taccatccaa agctggaatt tggcgggtgg aatgccttat tggcgagcat    3780
ctacatgctg ggatgagcac actttttctg gtgtacagca ataagtgtca gactcccctg    3840
ggaatggctt ctggacacat tagagatttt cagattacag cttcaggaca atatggacag    3900
tgggccccaa agctggccag acttcattat tccggatcaa tcaatgcctg gagcaccaag    3960
gagccctttt cttggatcaa ggtggatctg ttggcaccaa tgattattca cggcatcaag    4020
acccagggtg cccgtcagaa gttctccagc ctctacatct ctcagtttat catcatgtat    4080
agtcttgatg ggaagaagtg gcagacttat cgaggaaatt ccactggaac cttaatggtc    4140
ttctttggca atgtggattc atctgggata aacacaata ttttaaccc tccaattatt    4200 gctcgataca tccgtttgca cccaactcat tatagcattc gcagcactct tcgcatggag    4260
ttgatgggct gtgatttaaa tagttgcagc atgccattgg gaatggagag taaagcaata    4320
tcagatgcac agattactgc ttcatcctac tttaccaata tgtttgccac ctggtctcct    4380
tcaaaagctc gacttcacct ccaagggagg agtaatgcct ggagacctca ggtgaataat    4440
ccaaaagagt ggctgcaagt ggacttccag aagacaatga aagtcacagg agtaactact    4500
cagggagtaa aatctctgct taccagcatg tatgtgaagg agttcctcat ctccagcagt    4560
caagatggcc atcagtggac tctctttttt cagaatggca aagtaaaggt ttttcaggga    4620
aatcaagact ccttcacacc tgtggtgaac tctctagacc caccgttact gactcgctac    4680
cttcgaattc acccccagag ttgggtgcac cagattgccc tgaggatgga ggttctgggc    4740
tgcgaggcac aggacctcta ctgactcgag aataaaagat cagagctcta gagatctgtg    4800
tgttggtttt ttgtgtgcgg ccgcaggaac ccctagtgat ggagttggcc actccctctc    4860
tgcgcgctcg ctcgctcact gaggccgggc gaccaaaggt cgcccgacgc ccgggctttg    4920
cccgggcggc ctcagtgagc gagcgagcgc gcagctgcct gcaggacatg tgagcaaaag    4980
gccagcaaaa ggccaggaac cgtaaaaagg ccgcgttgct ggcgttttc cataggctcc    5040 gcccccctga cgagcatcac aaaaatcgac gctcaagtca gaggtggcga accccgacag    5100
gactataaag ataccaggcg tttccccctg gaagctccct cgtgcgctct cctgttccga    5160
```

-continued

```
ccctgccgct taccggatac ctgtccgcct ttctcccttc gggaagcgtg gcgctttctc    5220
atagctcacg ctgtaggtat ctcagttcgg tgtaggtcgt tcgctccaag ctgggctgtg    5280
tgcacgaacc ccccgttcag cccgaccgct gcgccttatc cggtaactat cgtcttgagt    5340 ccaacccgt aagacacgac ttatcgccac tggcagcagc cactggtaac aggattagca    5400
gagcgaggta tgtaggcggt gctacagagt tcttgaagtg gtggcctaac tacggctaca    5460
ctagaaggac agtatttggt atctgcgctc tgctgaagcc agttaccttc ggaaaaagag    5520
ttggtagctc ttgatccggc aaacaaacca ccgctggtag cggtggtttt tttgtttgca    5580
agcagcagat tacgcgcaga aaaaaggat ctcaagaaga tcctttgatc ttttctacgg     5640
ggtctgacgc tcagtggaac gaaaactcac gttaagggat tttggtcatg agattatcaa    5700
aaaggatctt cacctagatc cttttaaatt aaaaatgaag ttttaaatca atctaaagta    5760
tatatgagta aacttggtct gacagttacc aatgcttaat cagtgaggca cctatctcag    5820
cgatctgtct atttcgttca tccatagttg cctgactccc cgtcgtgtag ataactacga    5880
tacgggaggg cttaccatct ggccccagtg ctgcaatgat accgcgagac ccacgctcac    5940
cggctccaga tttatcagca ataaaccagc cagccggaag ggccgagcgc agaagtggtc    6000
ctgcaacttt atccgcctcc atccagtcta ttaattgttg ccgggaagct agagtaagta    6060
gttcgccagt taatagtttg cgcaacgttg ttgccattgc tacaggcatc gtggtgtcac    6120
gctcgtcgtt tggtatggct tcattcagct ccggttccca acgatcaagg cgagttacat    6180 gatccccat gttgtgcaaa aaagcggtta gctccttcgg tcctccgatc gttgtcagaa     6240
gtaagttggc cgcagtgtta tcactcatgg ttatggcagc actgcataat tctcttactg    6300
tcatgccatc cgtaagatgc ttttctgtga ctggtgagta ctcaaccaag tcattctgag    6360
aatagtgtat gcggcgaccg agttgctctt gcccggcgtc aatacgggat aataccgcgc    6420
cacatagcag aactttaaaa gtgctcatca ttggaaaacg ttcttcgggg cgaaaactct    6480
caaggatctt accgctgttg agatccagtt cgatgtaacc cactcgtgca cccaactgat    6540
cttcagcatc ttttactttc accagcgttt ctgggtgagc aaaaacagga aggcaaaatg    6600
ccgcaaaaaa gggaataagg gcgacacgga atgttgaat actcatactc ttcctttttc     6660
aatattattg aagcatttat cagggttatt gtctcatgag cggatacata tttgaatgta    6720
tttagaaaaa taaacaaata ggggttccgc gcacatttcc ccgaaaagtg ccacctgacg    6780
tctaagaaac cattattatc atgacattaa cctataaaaa taggcgtatc acgaggccct    6840
ttcgtctcgc gcgtttcggt gatgacggtg aaaacctctg acacatgcag ctcccggaga    6900
cggtcacagc ttgtctgtaa gcggatgccg ggagcagaca gcccgtcag ggcgcgtcag     6960 cgggtgttgg cgggtgtcgg ggctggctta actatgcggc atcagagcag attgtactga    7020
gagtgcacca taaaattgta acgttaata ttttgttaaa attcgcgtta aattttttgtt    7080 aaatcagctc attttttaac caataggccg aaatcggcaa aatcccttat aaatcaaaag    7140
aatagcccga atagggttg agtgttgttc cagtttggaa caagagtcca ctattaaaga    7200
acgtggactc caacgtcaaa gggcgaaaaa ccgtctatca gggcgatggc ccactacgtg    7260
aaccatcacc caaatcaagt ttttggggt cgaggtgccg taaagcacta aatcggaacc    7320
ctaaagggag cccccgattt agagcttgac ggggaaagcc ggcgaacgtg gcgagaaagg    7380
aagggaagaa agcgaaagga gcgggcgcta gggcgctggc aagtgtagcg gtcacgctgc    7440
gcgtaaccac cacacccgcc gcgcttaatg cgccgctaca gggcgcgtac tatggttgct    7500
ttgacgtatg cggtgtgaaa taccgcacag atgcgtaagg agaaaatacc gcatcaggcc    7560
```

```
gtaacctgtc ggatcaccgg aaaggacccg taaagtgata atgattatca tctacatatc    7620
acaacgtgcg tggaggccat caaaccacgt caaataatca attatgacgc aggtatcgta    7680
ttaattgatc tgcatcaact taacgtaaaa acaacttcag acaatacaaa tcagcgacac    7740
tgaatacggg gcaacctcat gtcaacgaag aacagaaccc gcagaacaac aacccgcaac    7800
atccgctttc ctaaccaaat gattgaacaa attaacatcg ctcttgagca aaaagggtcc    7860
gggaatttct cagcctgggt cattgaagcc tgccgtcgga gactaacgtc agaaaagaga    7920
gcatatacat caattaaaag tgatgaagaa tgaacatccc gcgttcttcc ctccgaacag    7980
gacgatattg taaattcact taattacgag ggcattgcag taattgagtt gcagttttac    8040
cactttcctg acagtgacag actgcgtgtt ggctctgtca cagactaaat agtttgaatg    8100
attagcagtt atggtgatca gtcaaccacc agggaataat ccttcatatt attatcgtgc    8160
ttcaccaacg ctgcctcaat tgctctgaat gcttccagag acaccttatg ttctatacat    8220
gcaattacaa catcagggta actcatagaa atggtgctat taagcatatt ttttacacga    8280
atcagatcca cggagggatc atcagcagat tgttctttat tcattttgtc gctccatgcg    8340
cttgctcttc atctagcggt taaaatatta cttcaaatct ttctgtatga agatttgagc    8400
acgttggcct tacatacatc tgtcggttgt atttccctcc agaatgccag caggaccgca    8460
ctttgttacg caaccaatac tattaagtga aacattcct  aatatttgac ataaatcatc    8520
aacaaaacac aaggaggtca gaccagattg aaacgataaa aacgataatg caaactacgc    8580
gccctcgtat cacatggaag gttttaccaa tggctcaggt tgccattttt aaagaaatat    8640
tcgatcaagt gcgaaaagat ttagactgtg aattgtttta ttctgaacta aaacgtcaca    8700
acgtctcaca ttatatttac tatctagcca cagataatat tcacatcgtg ttagaaaacg    8760
ataacaccgt gttaataaaa ggacttaaaa aggttgtaaa tgttaaattc tcaagaaaca    8820
cgcatcttat agaaacgtcc tatgataggt tgaaatcaag agaaatcaca tttcagcaat    8880
acagggaaaa tcttgctaaa gcaggagttt tccgatgggt tacaaatatc catgaacata    8940
aaagatatta ctataccttt gataattcat tactatttac tgagagcatt cagaacacta    9000
cacaaatctt tccacgctaa atcataacgt ccggtttctt ccgtgtcagc accggggcgt    9060
tggcataatg caatacgtgt acgcgctaaa ccctgtgtgc atcgttttaa ttattcccgg    9120
acactcccgc agagaagttc cccgtcaggg ctgtggacat agttaatccg ggaatacaat    9180
gacgattcat cgcacctgac atacattaat aaatattaac aatatgaaat ttcaactcat    9240
tgtttagggt ttgtttaatt ttctacacat acgattctgc gaacttcaaa aagcatcggg    9300
aataacacca tgaaaaaaat gctactcgct actgcgctgg ccctgcttat tacaggatgt    9360
gctcaacaga cgtttactgt tcaaaacaaa ccggcagcag tagcaccaaa ggaaaccatc    9420
acccatcatt tcttcgtttc tggaattggg cagaagaaaa ctgtcgatgc agccaaaatt    9480
tgtggcggcg cagaaaatgt tgttaaaaca gaaacccagc aaacattcgt aaatggattg    9540
ctcggtttta ttactttagg catttatact ccgctgaaag cgcgtgtgta ttgctcacaa    9600
taattgcatg agttgcccat cgcgatatgg gcaactctat ctgcactgct cattaatata    9660 cttctggggtt cctccagtt gttttttgcat agtgatcagc ctctctctga gggtgaaata    9720
atcccgttca gcggtgtctg ccagtcgggg ggaggctgca ttatccacgc cggaggcggt    9780
ggtggcttca cgcactgact gacagactgc tttgatgtgc aaccgacgac gaccagcggc    9840
aacatcatca cgcagagcat catttttcagc tttagcatca gctaactcct tcgtgtattt    9900
```

-continued

```
tgcatcgagc gcagcaacat cacgctgacg catctgcatg tcagtaattg ccgcgttcgc      9960
cagcttcagt tctctggcat ttttgtcgcg ctgggctttg taggtaatgg cgttatcacg     10020
gtaatgatta acagcccatg acaggcagac gatgatgcag ataaccagag cggagataat     10080
cgcggtgact ctgctcatac atcaatctct ctgaccgttc cgcccgcttc tttgaatttt     10140
gcaatcaggc tgtcagcctt atgctcgaac tgaccataac cagcgcccgg cagtgaagcc     10200
cagatattgc tgcaacggtc gattgcctga cggatatcac cacgatcaat cataggtaaa     10260
gcgccacgct ccttaatctg ctgcaatgcc acagcgtcct gacttttcgg agagaagtct     10320
ttcaggccaa gctgcttgcg gtaggcatcc caccaacggg aaagaagctg gtagcgtccg     10380
gcgcctgttg atttgagttt tgggtttagc gtgacaagtt tgcgagggtg atcggagtaa     10440
tcagtaaata gctctccgcc tacaatgacg tcataaccat gatttctggt tttctgacgt     10500
ccgttatcag ttccctccga ccacgccagc atatcgagga acgccttacg ttgattattg     10560
atttctacca tcttctactc cggcttttt agcagcgaag cgtttgataa gcgaaccaat     10620
cgagtcagta ccgatgtagc cgataaaacac gctcgttata taagcgagat tgctacttag     10680
tccggcgaag tcgagaaggt cacgaatgaa ccaggcgata atggcgcaca tcgttgcgtc     10740
gattactgtt tttgtaaacg caccgccatt atatctgccg cgaaggtacg ccattgcaaa     10800
cgcaaggatt gccccgatgc cttgttcctt tgccgcgaga atggcggcca acaggtcatg     10860
tttttctggc atcttcatgt cttaccccca ataaggggat ttgctctatt taattaggaa     10920
taaggtcgat tactgataga acaaatccag gctactgtgt ttagtaatca gatttgttcg     10980
tgaccgatat gcacgggcaa aacggcagga ggttgttagc gcgacctcct gccacccgct     11040
ttcacgaagg tcatgtgtaa aaggccgcag cgtaactatt actaatgaat tcaggacaga     11100
cagtggctac ggctcagttt gggttgtgct gttgctgggc ggcgatgacg cctgtacgca     11160
tttggtgatc cggttctgct tccggtattc gcttaattca gcacaacgga aagagcactg     11220
gctaaccagg ctcgccgact cttcacgatt atcgactcaa tgctcttacc tgttgtgcag     11280
atataaaaaa tcccgaaacc gttatgcagg ctctaactat tacctgcgaa ctgtttcggg     11340
attgcatttt gcagacctct ctgcctgcga tggttggagt tccagacgat acgtcgaagt     11400
gaccaactag gcggaatcgg tagtaagcgc cgcctctttt catctcacta ccacaacgag     11460
cgaattaacc catcgttgag tcaaatttac ccaatttat tcaataagtc aatatcatgc     11520
cgttaatatg ttgccatccg tggcaatcat gctgctaacg tgtgaccgca ttcaaaatgt     11580
tgtctgcgat tgactcttct ttgtggcatt gcaccaccag agcgtcatac agcggcttaa     11640
cagtgcgtga ccaggtgggt tgggtaaggt ttgggattag catcgtcaca gcgcgatatg     11700
ctgcgcttgc tggcatcctt gaatagccga cgcctttgca tcttccgcac tctttctcga     11760
caactctccc ccacagctct gttttggcaa tatcaaccgc acggcctgta ccatggcaat     11820
ctctgcatct tgccccggc gtcgcggcac tacggcaata atccgcataa gcgaatgttg     11880
cgagcacttg cagtaccttt gccttagtat ttccttcaag ctgcccctgc agg            11933
```

<210> SEQ ID NO 14
<211> LENGTH: 4999
<212> TYPE: DNA
<213> ORGANISM: Artificial Sequence
<220> FEATURE:
<223> OTHER INFORMATION: Description of Artificial Sequence: Synthetic

<400> SEQUENCE: 14

```
cgcccctgca ggcagctgcg cgctcgctcg ctcactgagg ccgcccgggc aaagcccggg       60
```

-continued

```
cgtcgggcga cctttggtcg cccggcctca gtgagcgagc gagcgcgcag agagggagtg     120
gccaactcca tcactagggg ttcctgcggc cgcacgcgtg gtggcgcggg gtaaactggg     180
aaagtgatgt cgtgtactgg ctccgccttt ttcccgaggg tgggggagaa ccgtatataa     240
gtgcagtagt cgccgtgaac gttcttttc gcaacgggtt tgccgccccg cggcaggtaa     300
gtgccaggga atgtttgttc ttaaatacca tcgctccagg gaatgtttgt tcttaaatac     360
catctactga cactgacatc cactttttct ttttctccac aggtatcgat ccaccatgca     420
aatagagctc tccacctgct tctttctgtg ccttttgcga ttctgcttta gtgccaccag     480
aagatactac ctgggtgcag tggaactgtc atgggactat atgcaaagtg atctcggtga     540
gctgcctgtg gacgcaagat ttcctcctag agtgccaaaa tcttttccat tcaacacctc     600
agtcgtgtac aaaaagactc tgtttgtaga attcacggat caccttttca acatcgctaa     660
gccaaggcca ccctggatgg gtctgctagg tcctaccatc caggctgagg tttatgatac     720
agtggtcatt acacttaaga acatggcttc ccatcctgtc agtcttcatg ctgttggtgt     780
atcctactgg aaagcttctg agggagctga atatgatgat cagaccagtc aaagggagaa     840
agaagatgat aaagtcttcc ctggtggaag ccatacatat gtctggcagg tcctgaaaga     900
gaatggtcca atggcctctg acccactgtg ccttacctac tcatatcttt ctcatgtgga     960
cctggtaaaa gacttgaatt caggcctcat ggagcccta ctagtatgta gagaagggag     1020
tctggccaag gaaaagacac agaccttgca caaatttata ctacttttg ctgtatttga    1080 tgaagggaaa agttggcact cagaaacaaa gaactccttg atgcaggata gggatgctgc    1140
atctgctcgg gcctggccta aaatgcacac agtcaatggt tatgtaaaca ggtctctgcc    1200
aggtctgatt ggatgccaca ggaaatcagt ctattggcat gtgattggaa tgggcaccac    1260
tcctgaagtg cactcaatat tcctcgaagg tcacacattt cttgtgagga accatcgcca    1320
ggcgtccttg gaaatctcgc caataacttt ccttactgct caaacactct tgatggacct    1380
tggacagttt ctactgtttt gtcatatctc ttcccaccaa catgatggca tggaagctta    1440
tgtcaaagta gacagctgtc cagaggaacc ccaactacga atgaaaaata atgaagaagc    1500
ggaagactat gatgatgatc ttactgattc tgaaatggat gtggtcaggt ttgatgatga    1560
caactctcct tcctttatcc aaattcgctc agttgccaag aagcatccta aaacttgggt    1620
acattacatt gctgctgaag aggaggactg ggactatgct cccttagtcc tcgcccccga    1680
tgacagaagt tataaaagtc aatatttgaa caatggccct cagcggattg gtaggaagta    1740
caaaaaagtc cgatttatgg catacacaga tgaaaccttt aagactcgtg aagctattca    1800
gcatgaatca ggaatcttgg gacctttact ttatgggaa gttggagaca cactgttgat    1860
tatatttaag aatcaagcaa gcagaccata taacatctac cctcacggaa tcactgatgt    1920
ccgtcctttg tattcaagga gattaccaaa aggtgtaaaa catttgaagg attttccaat    1980
tctgccagga gaaatattca aatataaatg gacagtgact gtagaagatg gccaactaa     2040 atcagatcct cggtgcctga cccgctatta ctctagtttc gttaatatgg agagagatct    2100
agcttcagga ctcattggcc ctctcctcat ctgctacaaa gaatctgtag atcaaagagg    2160
aaaccagata atgtcagaca agaggaatgt catcctgttt tctgtatttg atgagaaccg    2220
aagctggtac ctcacagaga atatacaacg cttctctccc aatccagctg gagtgcagct    2280
tgaggatcca gagttccaag cctccaacat catgcacagc atcaatggct atgtttttga    2340
tagtttgcag ttgtcagttt gtttgcatga ggtggcatac tggtacattc taagcattgg    2400
```

| | |
|---|---:|
| agcacagact gacttccttt ctgtcttctt ctctggatat accttcaaac acaaaatggt | 2460 |
| ctatgaagac acactcaccc tattcccatt ctcaggagaa actgtcttca tgtcgatgga | 2520 |
| aaacccaggt ctatggattc tggggtgcca caactcagac tttcggaaca gaggcatgac | 2580 |
| cgccttactg aaggtttcta gttgtgacaa gaacactggt gattattacg aggacagtta | 2640 |
| tgaagatatt tcagcatact tgctgagtaa aacaatgcc attgaaccaa gaagcttctc | 2700 |
| ccagaatcca ccagtcttga aacgccatca acgcgaaata actcgtacta ctcttcagtc | 2760 |
| agatcaagag gaaattgact atgatgatac catatcagtt gaaatgaaga aggaagattt | 2820 |
| tgacatttat gatgaggatg aaaatcagag cccccgcagc tttcaaaaga aaacacgaca | 2880 |
| ctattttatt gctgcagtgg agaggctctg ggattatggg atgagtagct ccccacatgt | 2940 |
| tctaagaaac agggctcaga gtggcagtgt ccctcagttc aagaaagttg ttttccagga | 3000 |
| atttactgat ggctcccttta ctcagccctt ataccgtgga gaactaaatg aacatttggg | 3060 |
| actcctgggg ccatatataa gagcagaagt tgaagataat atcatggtaa ctttcagaaa | 3120 |
| tcaggcctct cgtccctatt ccttctattc tagccttatt tcttatgagg aagatcagag | 3180 |
| gcaaggagca gaacctagaa aaaactttgt caagcctaat gaaaccaaaa cttacttttg | 3240 |
| gaaagtgcaa catcatatgg cacccactaa agatgagttt gactgcaaag cctgggctta | 3300 |
| tttctctgat gttgacctgg aaaaagatgt gcactcaggc ctgattggac cccttctggt | 3360 |
| ctgccacact aacacactga accctgctca tgggagacaa gtgacagtac aggaatttgc | 3420 |
| tctgttttc accatctttg atgagaccaa agctggtac ttcactgaaa atatggaaag | 3480 |
| aaactgcagg gctccctgca atatccagat ggaagatccc acttttaaag agaattatcg | 3540 |
| cttccatgca atcaatggct acataatgga tacactacct ggcttagtaa tggctcagga | 3600 |
| tcaaaggatt cgatggtatc tgctcagcat gggcagcaat gaaaacatcc attctattca | 3660 |
| tttcagtgga catgtgttca ctgtacgaaa aaaagaggag tataaaatgg cactgtacaa | 3720 |
| tctctatcca ggtgtttttg agacagtgga aatgttacca tccaaagctg gaatttggcg | 3780 |
| ggtggaatgc cttattggcg agcatctaca tgctgggatg agcacacttt ttctggtgta | 3840 |
| cagcaataag tgtcagactc ccctgggaat ggcttctgga cacattagag attttcagat | 3900 |
| tacagcttca ggacaatatg gacagtgggc cccaaagctg gccagacttc attattccgg | 3960 |
| atcaatcaat gcctggagca ccaaggagcc cttttcttgg atcaaggtgg atctgttggc | 4020 |
| accaatgatt attcacggca tcaagaccca gggtgcccgt cagaagttct ccagcctcta | 4080 |
| catctctcag tttatcatca tgtatagtct tgatgggaag aagtggcaga cttatcgagg | 4140 |
| aaattccact ggaaccttaa tggtcttctt tggcaatgtg gattcatctg ggataaaaca | 4200 |
| caatatttt aaccctccaa ttattgctcg atacatccgt ttgcacccaa ctcattatag | 4260 |
| cattcgcagc actcttcgca tggagttgat gggctgtgat ttaaatagtt gcagcatgcc | 4320 |
| attgggaatg gagagtaaag caatatcaga tgcacagatt actgcttcat cctactttac | 4380 |
| caatatgttt gccacctggt ctccttcaaa agctcgactt cacctccaag ggaggagtaa | 4440 |
| tgcctggaga cctcaggtga ataatccaaa agagtggctg caagtggact ccagaagac | 4500 |
| aatgaaagtc acaggagtaa ctactcaggg agtaaaatct ctgcttacca gcatgtatgt | 4560 |
| gaaggagttc ctcatctcca gcagtcaaga tggccatcag tggactctct ttttcagaa | 4620 |
| tggcaaagta aaggttttc agggaaatca agactccttc acacctgtgg tgaactctct | 4680 |
| agacccaccg ttactgactc gctaccttcg aattcacccc cagagttggg tgcaccagat | 4740 |
| tgccctgagg atggaggttc tgggctgcga ggcacaggac ctctactgac tcgagcctaa | 4800 |

```
taaaggaaat ttattttcat tgcaatagtg tgttggtttt ttgtgtgcgg ccgcaggaac    4860
ccctagtgat ggagttggcc actccctctc tgcgcgctcg ctcgctcact gaggccgggc    4920
gaccaaaggt cgcccgacgc ccgggctttg cccgggcggc ctcagtgagc gagcgagcgc    4980
gcagctgcct gcaggacat                                                 4999
```

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 15

```
Ser Phe Ser Gln Asn Pro Pro Val Leu Lys Arg His Gln Arg
 1               5                  10
```